(12) United States Patent
Yang et al.

(10) Patent No.: US 10,176,294 B2
(45) Date of Patent: Jan. 8, 2019

(54) ACCURATE TYPING OF HLA THROUGH EXOME SEQUENCING

(71) Applicants: THE BROAD INSTITUTE, INC., Cambridge, MA (US); WASHINGTON UNIVERSITY, St. Louis, MO (US)

(72) Inventors: Xiao Yang, Cambridge, MA (US); Chang Liu, Cambridge, MA (US); Michael C. Zody, Cambridge, MA (US); John D. Pfeifer, St. Louis, MI (US)

(73) Assignees: The Broad Institute, Inc., Cambridge, MA (US); Washington University, St. Louis, MO (US)

( * ) Notice: Subject to any disclaimer, the term of this patent is extended or adjusted under 35 U.S.C. 154(b) by 415 days.

(21) Appl. No.: 14/772,347

(22) PCT Filed: Mar. 12, 2014

(86) PCT No.: PCT/US2014/024555
§ 371 (c)(1),
(2) Date: Sep. 2, 2015

(87) PCT Pub. No.: WO2014/150924
PCT Pub. Date: Sep. 25, 2014

(65) Prior Publication Data
US 2016/0125128 A1    May 5, 2016

Related U.S. Application Data

(60) Provisional application No. 61/793,961, filed on Mar. 15, 2013.

(51) Int. Cl.
*G06F 19/18* (2011.01)
*G06N 3/12* (2006.01)
(Continued)

(52) U.S. Cl.
CPC .............. *G06F 19/18* (2013.01); *G06F 19/22* (2013.01); *G06F 19/28* (2013.01); *G06N 3/12* (2013.01); *G06N 5/04* (2013.01)

(58) Field of Classification Search
CPC ................................... G06N 3/00; G06N 3/12
See application file for complete search history.

(56) References Cited

U.S. PATENT DOCUMENTS

2010/0261189 A1    10/2010    Bentley et al.

FOREIGN PATENT DOCUMENTS

WO    2009049889 A1    4/2009

OTHER PUBLICATIONS

Wang, C. et al., "High-Throughput, High-fidelity HLA Genotyping With Deep Sequencing". Proceedings of the National Academy of Sciences, 2012, vol. 109, No. 22; pp. 8686-8681; abstract; p. 8677, first column, second paragraph to second column, fourth paragraph; p. 8678, first column, second paragraph to second column, second paragraph; p. 8679, second column, first paragraph to p. 8680, first column, third paragraph; DOI: 10.1073/pnas. 2206614109.

(Continued)

*Primary Examiner* — Cheung Lee
(74) *Attorney, Agent, or Firm* — Melissa Hunter-Ensor; Brian J. Assessor; Greenberg Traurig, LLP

(57) ABSTRACT

Embodiments of the present disclosure present bioinformatic systems, methods, for allelic HLA typing (as well as and computer readable media having instructions for performing methods of HLA typing) using, for example, Illumina exome-sequencing data (e.g., 101 basepair, paired-end reads).

19 Claims, 24 Drawing Sheets
Specification includes a Sequence Listing.

(51) Int. Cl.
    *G06F 19/22*         (2011.01)
    *G06F 19/28*         (2011.01)
    *G06N 5/04*          (2006.01)

(56) References Cited

OTHER PUBLICATIONS

Boegel, S. et al., "HLA Typing From RNA-Seq Sequence Reads". Genome Med. 2012, vol. 4, No. 12, p. 102; abstract p. 2, first column, second paragraph; p. 7, figure 2 caption; PMID: 23259685.
Notification of Transmittal of the International Search Report and the Written Opinion of the International Searching Authority of corresponding PCT/US2014/024555, dated Sep. 8, 2014, 15 pages.

```
allele₀      GCGGAGATCACACTGACCTCGCAGTGGGATGGGGAGGACCA          SEQ:
                                                                1
r₀           GCGGAGATCACACTGACCTGGCAGTG                         2
                           CCTCGCAGTGGGATGGGGAGGACCA    r₁      3 r'           GCGGAGATCACACTGACCTSGCAGTGGGATGGGGAGGACCA          4
r₂                 ACACTGACCTCGCAGTGGGATGG                      5 r"           GCGGAGATCACACTGACCTGCAGTGGGATGGGGAGGACCA           6

(a)

allele₁      GCGGAGATCACACTGACCTCGCAGTGGGATGGGGAGGACCA          7
r₀             CGGAGATCACACTGACC    AGTGGGATGGGGAGGACCA  r₁    8,9 r'             CGGAGATCACACTGACCNNNNAGTGGGATGGGGAGGACCA         10
r₂                   ACTGACCTGCAGTGGGAT                         11 allele₂      GCGGAGATCACACTGACCTGCAGTGGGATGGGGAGGACCA           12
r₀             CGGAGATCACACTGACC    AGTGGGATGGGGAGGACCA  r₁   13,14 r"             CGGAGATCACACTGACCNNNAGTGGGANGGGGAGGACCA          15
r₂                   ACTGACCTGCAGTGGGAT                         16

```
A*02:01:01:01    GCTCTCACTCCATGAGGTATTTCTTCACATCCGTGTCCCGGCCCGGCCGCGGGGAGCCCCGCTTCATCGCAGTGGGCT
A*02:11:01       GCTCTCACTCCATGAGGTATTTCTTCACATCCGTGTCCCGGCCCGGCCGCGGGGAGCCCCGCTTCATCGCAGTGGGCT
Contig i         GCTCTCACTCCATGAGGTATTTCTTCACATCCGTGTCCCGGCCCGGCCGCGGGGAGCCCCGCTTCATCGCAGTGGGCT
Contig j         GCTCTCACTCCATGAGGTATTTCTTCACATCCGTGTCCCGGCCCGGCCGCGGGGAGCCCCGCTTCATCGCAGTGGGCT A*02:01:01:01    ACGTGGACGACACGCAGTTCGTGCGGTTCGACAGCGACGCCGCGAGCCAGAGGATGGAGCCGCGGGCGCCGTGGATAG
A*02:11:01       ACGTGGACGACACGCAGTTCGTGCGGTTCGACAGCGACGCCGCGAGCCAGAGGATGGAGCCGCGGGCGCCGTGGATAG
Contig i         ACGTGGACGACACGCAGTTCGTGCGGTTCGACAGCGACGCCGCGAGCCAGAGGATGGAGCCGCGGGCGCCGTGGATAG
Contig j         ACGTGGACGACACGCAGTTCGTGCGGTTCGACAGCGACGCCGCGAGCCAGAGGATGGAGCCGCGGGCGCCGTGGATAG A*02:01:01:01    AGCAGGAGGGTCCGGAGTATTGGGACGGGGAGACACGGAAAGTGAAGGCCCACTCACAGACTCACCGAGTGGACCTGG
A*02:11:01       AGCAGGAGGGTCCGGAGTATTGGGACGGGGAGACACGGAAAGTGAAGGCCCACTCACAGATTGACCGAGTGGACCTGG
Contig i         AGCAGGAGGGTCCGGAGTATTGGGACGGGGAGACACGGAAAGTGAAGGCCCACTCACAGACTCACCGAGTGGACCTGG
Contig j         AGCAGGAGGGTCCGGAGTATTGGGACGGGGAGACACGGAAAGTGAAGGCCCACTCACAGATTGACCGAGTGGACCTGG A*02:01:01:01    GGACCCTGCGCGGCTACTACAACCAGAGCGAGGCCG        SEQ ID NO: 17
A*02:11:01       GGACCCTGCGCGGCTACTACAACCAGAGCGAGGCCG        SEQ ID NO: 18
Contig i         GGACCCTGCGCGGCTACTACAACCAGAGCGAGGCCG        SEQ ID NO: 19
Contig j         GGACCCTGCGCGGCT---------------------        SEQ ID NO: 20

(a)

C*04:01:01:01    CCAGCAACAGTGCCCAGGGCTCTGATGAGTCTCTCATCGCTTGTAAAG    SEQ ID NO: 21
A*04:30          CCACCAACAGTGCCCAGGGCTCTGATGAGTCTCTCATCGCTTGTAAAG    SEQ ID NO: 22
Contig i         CCAGCAACAGTGCCCAGGGCTCTGATGAGTCTCTCATCGCTTGTAAAG    SEQ ID NO: 23

|  | | SEQ: |
|---|---|---|
| allele₀ | GCGGAGATCACACTGACCTCGCAGTGGGATGGGGAGGACCA | 24 |
| allele₁ | GCGGAGATCACACTGACCTGGCAGTGGGATGGGGAGGACCA | 25 |
| contigₐ | GCGGAGATCACACTGACCTCGCAGTGGGATGGGGAGGACCA | 26 |
| contig_b | GCGGAGATCACACTGACCNNNCAGTGGGATGGGGAGGACCA | 27 |

(a)

| Candidate Alleles | Exon1 | Exon2 | Exon3 | Exon4 |
|---|---|---|---|---|
| B*55:02:01 | A | A | A | A |
| B*56:11 | A | A | B | A |
| B*35:03:01 | B | B | B | B |
| B*35:60 | B | B | A | A |

Supplementary Table 1. Sequences of typed HLA genes included in the reference*

| Genes† | gDNA sequences | | | cDNA sequences | | |
|---|---|---|---|---|---|---|
| | Count | Median length (bp) | Range (bp) | Count | Median length (bp) | Range (bp) |
| HLA-A | 112 | 3332.5 | 2903 - 3518 | 1884 | 546 | 540 - 1163 |
| HLA-B | 149 | 3312 | 1208 - 3340 | 2489 | 546 | 531 - 1208 |
| HLA-C | 101 | 3343 | 2700 - 3368 | 1382 | 546 | 544 - 1197 |
| HLA-DRB1 | 26 | 13463.5 | 10299 - 16120 | 1092 | 270 | 222 - 801 |
| HLA-DQB1 | 18 | 7107 | 6800 - 7480 | 165 | 270 | 148 - 810 |

*Based on IMGT/HLA Database Release 3.8.
†The other off-target genes in the reference include DMA, DMB, DOA, DOB, DPA1, DPB1, DQA1, DRA, DRB3, DRB4, DRB5, E, F, G, H, J, K, L, MICA, MICB, P, TAP1, TAP2, V. They are less polymorphic compared to the HLA genes being typed, and both gDNA and cDNA sequences available are included.

Figure 11

Supplementary Table 2. Characteristics of exome-seq data used for *in silico* HLA typing

| Sample | Run ID | Study* | Sequencing facility† | Population | Country | SureSelect kit | Instrument | Read count | Exome coverage (≥10X) |
|---|---|---|---|---|---|---|---|---|---|
| HG01756 | SRR359102 | 1000 Genomes | WUGI | Iberian | Spain | V2 | GAIIx | 190844780 | 97% |
| HG01757 | SRR359108 | 1000 Genomes | WUGI | Iberian | Spain | V2 | GAIIx | 162640934 | 97% |
| HG01872 | SRR359298 | 1000 Genomes | WUGI | Kinh | Vietnam | V2 | GAIIx | 203129930 | 97% |
| HG01873 | SRR359295 | 1000 Genomes | WUGI | Kinh | Vietnam | V2 | GAIIx | 203842382 | 97% |
| HG01888 | SRR360655 | 1000 Genomes | WUGI | African | Barbados | V2 | GAIIx | 182159862 | 97% |
| HG01950 | SRR360288 | 1000 Genomes | WUGI | Peruvian | Peru | V2 | GAIIx | 192525408 | 96% |
| HG01966 | SRR360391 | 1000 Genomes | WUGI | Peruvian | Peru | V2 | GAIIx | 193939086 | 96% |
| HG02334 | SRR360148 | 1000 Genomes | WUGI | African | Barbados | V2 | GAIIx | 174583382 | 97% |
| HG02057 | SRR358301 | 1000 Genomes | WUGI | Kinh | Vietnam | V2 | GAIIx | 204851286 | 97% |
| NA20313 | SRR359088 | 1000 Genomes | WUGI | African | USA | V2 | GAIIx | 194802915 | 98% |
| NA20313‡ | SRR359108 | 1000 Genomes | WUGI | African | USA | V2 | GAIIx | 195282918 | 98% |
| NA18507 | 0635_7_ATCGAGC | Internal validation | GTAC | Yoruba | Nigeria | V3 50 Mb | HiSeq2000 | 132893768 | 96% |
| NA19129 | 0635_6_CACGTCC | Internal validation | GTAC | Yoruba | Nigeria | V3 50 Mb | HiSeq2000 | 206046924 | 97% |
| NA19240 | 0635_7_TACTCTA | Internal validation | GTAC | Yoruba | Nigeria | V3 50 Mb | HiSeq2000 | 189722418 | 97% |
| NA19240‡ | 0635_4_CTCAATG | Internal validation | GTAC | Yoruba | Nigeria | V3 50 Mb | HiSeq2000 | 177344782 | 96% |

*1000 Genomes project: http://ftp.1000genomes.ebi.ac.uk/1000genomes/ftp/data/; raw data from the internal validation study are available upon request.
†WUGI, Washington University Genome Institute; GTAC, Genome Technology Access Center at Washington University. All samples were sequenced as paired-end reads (2 X 101 bp).
‡Duplicate sequencing of NA20313 and NA19240.

Supplementary Table 4. A sample report generated by ALTHLATES (for HG01757, HLA-DQB1)

| Name | HD | Aln_len | cDNA_len | Similarity | Avg_cov | Missing Exons (ID, len) ; mismatches (ID, pos) |
|---|---|---|---|---|---|---|
| DQB1*03:03:02:03 | 0 | 772 | 786 | 1 | 134.253 | (5, 0) (6, 14) |
| DQB1*03:03:02:02 | 0 | 772 | 786 | 1 | 134.253 | (5, 0) (6, 14) |
| DQB1*03:03:02:01 | 0 | 772 | 786 | 1 | 134.253 | (5, 0) (6, 14) |
| DQB1*02:01:01 | 0 | 772 | 786 | 1 | 144.622 | (5, 0) (6, 14) |
| DQB1*02:02 | 1 | 772 | 786 | 0.998705 | 144.622 | (5, 0) (6, 14)  (3, 121) |
| DQB1*03:02:01 | 1 | 772 | 786 | 0.998705 | 134.253 | (5, 0) (6, 14)  (2, 157) |
| DQB1*03:31 | 1 | 618 | 618 | 0.998382 | 147.324 | (1, 0) (5, 0) (6, 0)  (3, 63) |
| DQB1*03:43 | 1 | 552 | 552 | 0.998188 | 154.324 | (1, 0) (4, 0) (5, 0) (6, 0)  (3, 141) |
| DQB1*03:41 | 1 | 552 | 552 | 0.998188 | 154.324 | (1, 0) (4, 0) (5, 0) (6, 0)  (2, 120) |
| DQB1*03:39 | 1 | 552 | 552 | 0.998188 | 154.324 | (1, 0) (4, 0) (5, 0) (6, 0)  (3, 98) |
| DQB1*03:38 | 1 | 552 | 552 | 0.998188 | 154.324 | (1, 0) (4, 0) (5, 0) (6, 0)  (2, 75) |
| DQB1*03:30 | 1 | 552 | 552 | 0.998188 | 154.324 | (1, 0) (4, 0) (5, 0) (6, 0)  (2, 15) |
| DQB1*03:03:04 | 1 | 552 | 552 | 0.998188 | 154.324 | (1, 0) (4, 0) (5, 0) (6, 0)  (3, 224) |
| DQB1*02:01:04 | 1 | 552 | 552 | 0.998188 | 173.219 | (1, 0) (4, 0) (5, 0) (6, 0)  (2, 194) |
| DQB1*02:01:05 | 1 | 552 | 552 | 0.998188 | 173.219 | (1, 0) (4, 0) (5, 0) (6, 0)  (2, 206) |
| DQB1*02:07 | 1 | 552 | 552 | 0.998188 | 173.219 | (1, 0) (4, 0) (5, 0) (6, 0)  (2, 229) |
| DQB1*02:04 | 1 | 552 | 552 | 0.998188 | 173.219 | (1, 0) (4, 0) (5, 0) (6, 0)  (3, 123) |
| DQB1*03:33 | 1 | 522 | 522 | 0.998084 | 149.414 | (1, 0) (4, 0) (5, 0) (6, 0)  (3, 156) |
| DQB1*03:34 | 1 | 522 | 522 | 0.998084 | 149.414 | (1, 0) (4, 0) (5, 0) (6, 0)  (2, 45) |
| DQB1*03:32 | 2 | 552 | 552 | 0.996377 | 154.324 | (1, 0) (4, 0) (5, 0) (6, 0)  (2, 157) (3, 138) |
| DQB1*02:06 | 2 | 552 | 552 | 0.996377 | 173.219 | (1, 0) (4, 0) (5, 0) (6, 0)  (3, 121) (3, 225) |

----------- Candidate Allelic Pairs -----------

| Name | HD | Aln_len | cDNA_len | Similarity | Avg_cov | Missing Exons (ID, len) ; mismatches (ID, pos) |
|---|---|---|---|---|---|---|
| DQB1*03:03:02:03 | 0 | 772 | 786 | 1 | 134.253 | (5, 0) (6, 14) |
| DQB1*03:03:02:02 | 0 | 772 | 786 | 1 | 134.253 | (5, 0) (6, 14) |
| DQB1*03:03:02:01 | 0 | 772 | 786 | 1 | 134.253 | (5, 0) (6, 14) |
| DQB1*02:01:01 | 0 | 772 | 786 | 1 | 144.622 | (5, 0) (6, 14) |

----------- Inferred Allelic Pairs -----------

| | | |
|---|---|---|
| DQB1*03:03:02:03 | DQB1*02:01:01 | 0 |
| DQB1*03:03:02:02 | DQB1*02:01:01 | 0 |
| DQB1*03:03:02:01 | DQB1*02:01:01 | 0 |

HD: Hamming distance.
Aln_len: alignment length, number of cDNA bases supported by contigs.
cDNA_len: total length of cDNA of an allele.
Avg_cov: average coverage for an allele.
Missing Exons (ID, len): ID, the identity of a exon not considered for calculation of Hamming distance, len, length of the indicated exon as documented in the IMGT/HLA database.
mismatches(ID, pos): the position (pos) of a mismatch in the exon of indicated identity (id) when compared to its best hit in contigs.

Figure 15B
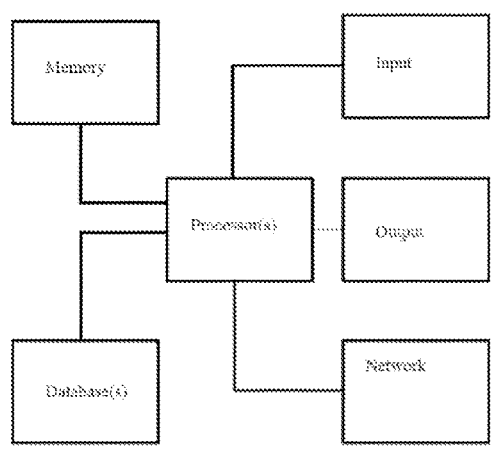
FIGURE 16
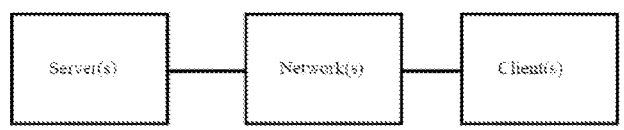
FIGURE 17

SEQUENCE LISTING

<160> NUMBER OF SEQ ID NOS: 27

<210> SEQ ID NO 1
<211> LENGTH: 41
<212> TYPE: DNA
<213> ORGANISM: Artificial Sequence
<220> FEATURE:
<223> OTHER INFORMATION: ambiguous sequence example

<400> SEQUENCE: 1
gcggagatca cactgacctc gcagtgggat ggggaggacc a          41

<210> SEQ ID NO 2
<211> LENGTH: 26
<212> TYPE: DNA
<213> ORGANISM: artificial
<220> FEATURE:
<223> OTHER INFORMATION: ambiguous sequence example

<400> SEQUENCE: 2
gcggagatca cactgacctg gcagtg                           26

<210> SEQ ID NO 3
<211> LENGTH: 25
<212> TYPE: DNA
<213> ORGANISM: artificial
<220> FEATURE:
<223> OTHER INFORMATION: ambiguous sequence example

<400> SEQUENCE: 3
cctcgcagtg ggatggggag gacca                            25

<210> SEQ ID NO 4
<211> LENGTH: 41
<212> TYPE: DNA
<213> ORGANISM: artificial
<220> FEATURE:
<223> OTHER INFORMATION: ambiguous sequence example

<400> SEQUENCE: 4
gcggagatca cactgaccts gcagtgggat ggggaggacc a          41

```
<210> SEQ ID NO 5
<211> LENGTH: 23
<212> TYPE: DNA
<213> ORGANISM: artificial
<220> FEATURE:
<223> OTHER INFORMATION: ambiguous sequence example

<400> SEQUENCE: 5
acactgacct cgcagtggga tgg                                              23

<210> SEQ ID NO 6
<211> LENGTH: 41
<212> TYPE: DNA
<213> ORGANISM: artificial
<220> FEATURE:
<223> OTHER INFORMATION: ambiguous sequence example

<400> SEQUENCE: 6
gcggagatca cactgacctc gcagtgggat ggggaggacc a                          41

<210> SEQ ID NO 7
<211> LENGTH: 41
<212> TYPE: DNA
<213> ORGANISM: artificial
<220> FEATURE:
<223> OTHER INFORMATION: ambiguous sequence example

<400> SEQUENCE: 7
gcggagatca cactgacctc gcagtgggat ggggaggacc a                          41

<210> SEQ ID NO 8
<211> LENGTH: 17
<212> TYPE: DNA
<213> ORGANISM: artificial
<220> FEATURE:
<223> OTHER INFORMATION: ambiguous sequence example

<400> SEQUENCE: 8
cggagatcac actgacc                                                     17

<210> SEQ ID NO 9
<211> LENGTH: 19
<212> TYPE: DNA
<213> ORGANISM: artificial
<220> FEATURE:
<223> OTHER INFORMATION: ambiguous sequence example

<400> SEQUENCE: 9
agtgggatgg ggaggacca                                                   19

<210> SEQ ID NO 10
<211> LENGTH: 40
<212> TYPE: DNA
<213> ORGANISM: artificial
<220> FEATURE:
<223> OTHER INFORMATION: ambiguous sequence example
<220> FEATURE:
<221> NAME/KEY: misc_feature
<222> LOCATION: (18)..(21)
<223> OTHER INFORMATION: Wherein N may be A or G or T or C

<400> SEQUENCE: 10
cggagatcac actgaccnnn nagtgggatg gggaggacca                            40
```

```
<210> SEQ ID NO 11
<211> LENGTH: 18
<212> TYPE: DNA
<213> ORGANISM: artificial
<220> FEATURE:
<223> OTHER INFORMATION: ambiguous sequence example

<400> SEQUENCE: 11
actgacctgc agtgggat                                                     18

<210> SEQ ID NO 12
<211> LENGTH: 40
<212> TYPE: DNA
<213> ORGANISM: artificial
<220> FEATURE:
<223> OTHER INFORMATION: ambiguous sequence example

<400> SEQUENCE: 12
gcggagatca cactgacctg cagtgggatg gggaggacca                             40

<210> SEQ ID NO 13
<211> LENGTH: 17
<212> TYPE: DNA
<213> ORGANISM: artificial
<220> FEATURE:
<223> OTHER INFORMATION: ambiguous sequence example

<400> SEQUENCE: 13
cggagatcac actgacc                                                      17

<210> SEQ ID NO 14
<211> LENGTH: 19
<212> TYPE: DNA
<213> ORGANISM: artificial
<220> FEATURE:
<223> OTHER INFORMATION: ambiguous sequence example

<400> SEQUENCE: 14
agtgggatgg ggaggacca                                                    19

<210> SEQ ID NO 15
<211> LENGTH: 39
<212> TYPE: DNA
<213> ORGANISM: artificial
<220> FEATURE:
<223> OTHER INFORMATION: ambiguous sequence example
<220> FEATURE:
<221> NAME/KEY: misc_feature
<222> LOCATION: (18)..(20)
<223> OTHER INFORMATION: Wherein N may be A or G or T or C

<400> SEQUENCE: 15
cggagatcac actgaccnnn agtgggatgg ggaggacca                              39

<210> SEQ ID NO 16
<211> LENGTH: 18
<212> TYPE: DNA
<213> ORGANISM: artificial
<220> FEATURE:
<223> OTHER INFORMATION: ambiguous sequence example

<400> SEQUENCE: 16
actgacctgc agtgggat                                                     18
```

```
<210> SEQ ID NO 17
<211> LENGTH: 270
<212> TYPE: DNA
<213> ORGANISM: artificial
<220> FEATURE:
<223> OTHER INFORMATION: ambiguous sequence example

<400> SEQUENCE: 17
gctctcactc catgaggtat ttcttcacat ccgtgtcccg gcccggccgc ggggagcccc      60
gcttcatcgc agtgggctac gtggacgaca cgcagttcgt gcggttcgac agcgacgccg     120
cgagccagag gatggagccg cgggcgccgt ggatagagca ggagggtccg gagtattggg     180
acggggagac acggaaagtg aaggcccact cacagactca ccgagtggac ctggggaccc     240
tgcgcggcta ctacaaccag agcgaggccg                                      270

<210> SEQ ID NO 18
<211> LENGTH: 270
<212> TYPE: DNA
<213> ORGANISM: artificial
<220> FEATURE:
<223> OTHER INFORMATION: ambiguous sequence example

<400> SEQUENCE: 18
gctctcactc catgaggtat ttcttcacat ccgtgtcccg gcccggccgc ggggagcccc      60
gcttcatcgc agtgggctac gtggacgaca cgcagttcgt gcggttcgac agcgacgccg     120
cgagccagag gatggagccg cgggcgccgt ggatagagca ggagggtccg gagtattggg     180
acggggagac acggaaagtg aaggcccact cacagattga ccgagtggac ctggggaccc     240
tgcgcggcta ctacaaccag agcgaggccg                                      270

<210> SEQ ID NO 19
<211> LENGTH: 270
<212> TYPE: DNA
<213> ORGANISM: artificial
<220> FEATURE:
<223> OTHER INFORMATION: ambiguous sequence example

<400> SEQUENCE: 19
gctctcactc catgaggtat ttcttcacat ccgtgtcccg gcccggccgc ggggagcccc      60
gcttcatcgc agtgggctac gtggacgaca cgcagttcgt gcggttcgac agcgacgccg     120
cgagccagag gatggagccg cgggcgccgt ggatagagca ggagggtccg gagtattggg     180
acggggagac acggaaagtg aaggcccact cacagactca ccgagtggac ctggggaccc     240
tgcgcggcta ctacaaccag agcgaggccg                                      270

<210> SEQ ID NO 20
<211> LENGTH: 249
<212> TYPE: DNA
<213> ORGANISM: artificial
<220> FEATURE:
<223> OTHER INFORMATION: ambiguous sequence example

<400> SEQUENCE: 20
gctctcactc catgaggtat ttcttcacat ccgtgtcccg gcccggccgc ggggagcccc      60
gcttcatcgc agtgggctac gtggacgaca cgcagttcgt gcggttcgac agcgacgccg     120
cgagccagag gatggagccg cgggcgccgt ggatagagca ggagggtccg gagtattggg     180
acggggagac acggaaagtg aaggcccact cacagattga ccgagtggac ctggggaccc     240
tgcgcggct                                                             249
```

<210> SEQ ID NO 21
<211> LENGTH: 48
<212> TYPE: DNA
<213> ORGANISM: artificial
<220> FEATURE:
<223> OTHER INFORMATION: ambiguous sequence example

<400> SEQUENCE: 21
ccagcaacag tgcccagggc tctgatgagt ctctcatcgc ttgtaaag                48

<210> SEQ ID NO 22
<211> LENGTH: 48
<212> TYPE: DNA
<213> ORGANISM: artificial
<220> FEATURE:
<223> OTHER INFORMATION: ambiguous sequence example

<400> SEQUENCE: 22
ccaccaacag tgcccagggc tctgatgagt ctctcatcgc ttgtaaag                48

<210> SEQ ID NO 23
<211> LENGTH: 48
<212> TYPE: DNA
<213> ORGANISM: artificial
<220> FEATURE:
<223> OTHER INFORMATION: ambiguous sequence example

<400> SEQUENCE: 23
ccagcaacag tgcccagggc tctgatgagt ctctcatcgc ttgtaaag                48

<210> SEQ ID NO 24
<211> LENGTH: 41
<212> TYPE: DNA
<213> ORGANISM: artificial
<220> FEATURE:
<223> OTHER INFORMATION: ambiguous sequence example

<400> SEQUENCE: 24
gcggagatca cactgacctc gcagtgggat ggggaggacc a                      41

<210> SEQ ID NO 25
<211> LENGTH: 41
<212> TYPE: DNA
<213> ORGANISM: artificial
<220> FEATURE:
<223> OTHER INFORMATION: ambiguous sequence example

<400> SEQUENCE: 25
gcggagatca cactgacctg gcagtgggat ggggaggacc a                      41

<210> SEQ ID NO 26
<211> LENGTH: 41
<212> TYPE: DNA
<213> ORGANISM: artificial
<220> FEATURE:
<223> OTHER INFORMATION: ambiguous sequence example

<400> SEQUENCE: 26
gcggagatca cactgacctc gcagtgggat ggggaggacc a                      41

<210> SEQ ID NO 27
<211> LENGTH: 41
<212> TYPE: DNA
<213> ORGANISM: artificial
<220> FEATURE:
<223> OTHER INFORMATION: ambiguous sequence example

```
<220> FEATURE:
<221> NAME/KEY: misc_feature
<222> LOCATION: (19)..(21)
<223> OTHER INFORMATION: Wherein N may be A or G or T or C

<400> SEQUENCE: 27
gcggagatca cactgaccnn ncagtgggat ggggaggacc a                    41
```

ACCURATE TYPING OF HLA THROUGH EXOME SEQUENCING

STATEMENT REGARDING FEDERALLY SPONSORED RESEARCH & DEVELOPMENT

This invention was made with government support under Grant No. HHSN272200900018C awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 2, 2015, is named "364950_1035US1_00070_Sequencelisting.txt" and is 6.84 KB in size.

FIELD OF THE DISCLOSURE

Embodiments of the present disclosure are directed to Human leukocyte antigen (HLA) detection at the allelic level using sequencing data.

BACKGROUND

Allelic HLA typing refers to sequencing-based typing to determine variations in coding DNA sequences that alter the protein sequences. This is also commonly referred to as high resolution typing or four-digit typing. There are also alleles that bear synonymous mutations and mutations within non-coding DNA, but resolution of these alleles is rarely necessary in clinical practice. In the IMGT/HLA database (1), the majority of HLA alleles are represented by full-length or partial complementary DNA (cDNA) sequences. Some HLA alleles have both cDNA and genomic DNA (gDNA) sequences deposited in the database. For simplicity, we also term a cDNA and/or gDNA sequence of an HLA gene an allele.

HLA typing at the allelic level is typically performed by Sanger sequencing of selected exons of Class I genes (HLA-A, -B and -C) and Class II genes (HLA-DRB1 and -DQB1). HLA typing using exome sequencing (exome-seq) data is in its infancy. Currently, there is no methodology available to perform HLA typing at the allelic level with the necessary accuracy given the typical read length of Illumina and the level of polymorphism within the region. Indeed, a recent report(2) demonstrated that allelic HLA typing is challenging to obtain from Illumina exome-seq data even at high coverage.

The nomenclature of HLA alleles follows the guidelines from the WHO Nomenclature Committee for Factors of the HLA System (http://hla.alleles.org/nomenclature/naming.html).

SUMMARY OF THE EMBODIMENTS

Embodiments of the present disclosure present bioinformatic systems, methods, for allelic HLA typing (as well as and computer readable media having instructions for performing methods of HLA typing) using, for example, Illumina exome-sequencing data (e.g., 101 basepair, paired-end reads).

Embodiments of the present disclosure overcome a major bioinformatic hurdle in applying targeted Illumina sequencing to allelic HLA typing. For example, qualified exome-seq datasets from research projects can be analyzed to revisit HLA-disease associations with allelic resolution. In addition, some embodiments provide a way to deep sequencing of captured HLA genes alone rather than the whole exome, which enables multiplexing samples for high-throughput typing of bone marrow donors at reduced cost. In some embodiments, the HLA genes can also be bundled with existing oncogene panels(3) for targeted Illumina sequencing in order to prepare leukemic patients for transplantation while characterizing the molecular profiles of their diseases.

Previous methods have relied on the assumption that more reads align to the correct alleles(4) (2). However, this assumption does not wholly apply to exome-sequencing data, as there are often large differences in the coverage of different exons (FIG. 2a, FIG. 7). In some embodiments of the present disclosure, a set of contigs may be assembled from target (e.g. HLA-A) specific reads to substantially represent haplotype exons of the target gene (in some embodiments, fully represent haplotype exons of the target gene). In some embodiments, the target specific reads may be obtained using two stages of filtering. For example, exome-sequencing data may be first filtered against alleles of HLA genes obtained from the, for example, IMGT/HLA database (FIG. 11), to narrow the searching space.

In some embodiments, due to homology between alleles of different HLA genes, reads that concurrently align to target and off-target genes may be filtered, as these reads may introduce ambiguities to an assembly. It has been observed that up to 9% of reads are multi-mapped, where HLA-A and -DRB1 have higher percentages of multi-mapped reads compared with HLA-B, -C, and -DQB 1 genes.

Unlike existing short read assemblers (5) (6), in some embodiments, distinct strategies to facilitate sequence assembly in the highly polymorphic HLA region are adopted. For example, in some embodiments, a read pair is first converted to a haplotype sequence when both ends are aligned to the same reference allele. This is accomplished in order to effectively elongate the input reads. Furthermore, because many fragments may have sequencing gaps between both ends, in some embodiments, degenerate bases are used as placeholders at uncertain positions in the contig. These gaps may be resolved based on information from reads merged into the contig at a later point, for example (FIG. 3). In some embodiments, degenerate bases can also serve as an indicator of insufficient read support, which can be factored in during allelic pair inference (for example). Additionally, assembly of contigs sharing longer substrings with higher frequencies may be prioritized in some embodiments.

In some embodiments, identification of relevant alleles whose exons should match the contigs assembled at a previous step may be accomplished. In such embodiments, the quality of an allele may be measured by, for example, summation of Hamming distances between individual exons and their best match in the contigs. During a matching process, for example, sequence similarity over the length of matching substrings (FIG. 4) may be prioritized. This may be done for at least one of two considerations. First, in some embodiments, alleles with nearly identical sequences require differentiation. Second, exons may be only partially sequenced which results in degenerate bases in the contig. Accordingly, in some embodiments, candidate alleles are qualified within a hamming distance of, for example, 2, which allows inclusion of potential novel alleles closely related to existing alleles.

In some embodiments, an additional step for an HLA typing process includes, for example, inferring homozygous and/or heterozygous allelic pairs by considering all possible allelic pairs and checking if the allelic pairs are consistent with the data as represented by contigs. To achieve this, in some embodiments, the principle of parsimony is utilized which ensures allelic pairs, fully supported by the data, may be prioritized over pairs consistent with but not fully supported by the data (FIG. 5a). The final allelic pairs, in some embodiments, should also explain as much of the information present in the data as possible (FIG. 5b). Meanwhile, phasing information among discrete exons may be inferred, in some embodiments (FIG. 5b) since exome-seq may not fully capture introns.

Accordingly, in some embodiments of the present disclosure, a computer-implemented method for HLA typing is provided, with the method comprising one or more of the following steps (and in some embodiments, a plurality of the steps, and in some embodiments, all of the following steps): accessing sequencing data that contains HLA information stored in one or more databases, accessing HLA sequences of alleles of one or more HLA genes and the multiple sequence alignment of these HLA sequences stored in one or more databases, and searching for target-specific reads/read-pairs from the sequencing data. Searching may comprise first filtering the sequencing data against HLA sequences to obtain a first set of reads/read-pairs aligned to these sequences, and second filtering the first set to eliminate reads/read-pairs concurrently aligned to both sequences of the target HLA gene and off-target HLA genes to obtain a second set of target HLA reads/read-pairs. The method may further include assembling a plurality of reads/read-pairs uniquely aligned to a target HLA gene into one or more contigs. Assembling may comprise merging read-pairs having both ends aligned to the same reference allele to form single-reads/haplotype sequences, and assembling one or more contigs from the haplotype sequences. The assembly of contigs having longer substrings with higher frequencies may be prioritized. The method may also include identifying relevant target alleles having exons matching the assembled contigs, where identifying may comprise decomposing target alleles into exons, calculating the Hamming distance (HD) between individual target allele exons and corresponding best matches from the assembled contigs, and prioritizing sequence similarity over the length of matching substrings between the contigs and the target allele exons.

In some embodiments, relevant alleles within a first predetermined HD are selected as candidate alleles.

In some embodiments, the HLA typing method may also include inferring at least one of homozygous or heterozygous allelic pairs from the candidate alleles, where inferring may comprise selecting alleles from the candidate alleles having a HD less than a second predetermined distance.

In some embodiments, first filtering may include soft-clipping during alignment.

In some embodiments, a read/read-pair may be included in the first set upon the read/read-pair having a high quality suffix-prefix alignment with the HLA sequences of known alleles.

In some embodiments, HLA typing method may further include dividing paired-end reads that align to the same known allele into substrings, where upon the prefix and suffix of the paired-end reads overlapping, and the substrings are substantially equal in length and not empty, the read-pairs are merged to form single-reads/haplotype sequences. Additionally, upon one read of a read-pair merging at a position including a sequencing error, degenerate bases may be encoded in the merged haplotype sequence, as well as upon the overlap being empty, the gap between the read-pair is encoded with degenerate bases. In some embodiments, upon degenerate bases being present and their intersection being not empty, the base at the intersection is used to assemble the contig.

Assembly of the contigs from the haplotype sequences, in some embodiments, may comprise merging haplotype sequences upon the haplotype sequences sharing common l-mers. l may be initially set to the value of the maximum read length and then iteratively decreased by a fixed amount until a minimum threshold is reached.

Haplotype sequences containing sequencing errors may comprise reads/read-pairs having low frequency k-mers, and, in some embodiments, such read/read-pairs may be eliminated from assembly into contigs.

In some embodiments, assembly includes decomposing haplotype sequences into a set of l-mers and sorting the results in a decreasing order of frequency. For example, for each l-mer in the sorted list, contigs which share a specific l-mer are assembled.

Other embodiments may include one or more of the following features, at least one or more of which can stand on their own as separate embodiments, or combined with any number of the above embodiments:
  relative positions of any two contigs may be determined in constant time by matching the l-mer;
  insertion/deletion errors may be disallowed during contig assembly;
  reads/read-pairs may be merged upon being concordant at each alignment position;
  the frequency of bases of each contig for each position is accrued for identifying insufficient exon capture or sequencing errors during assembly, where base regions of any contig having low base support may be replaced with a degenerative base, and where upon a prefix or suffix of a contig is a string of degenerative bases, assembly further comprises trimming the string;
  contig assembly may be carried out iteratively;
  tracking at least one of the removal of previously assembled contigs and the creation of new contigs, where tracking may comprise a union-find algorithm;
  an allele may be excluded from the candidate list upon the allele including an exon with no alignment found in the contigs;
  candidate alleles may comprise alleles with HD of 0, upon such alleles corresponding to two or more types of protein coding sequences;
  e candidate alleles may comprise alleles with a HI) of less than or equal to a predetermined threshold; and/or
  selecting two alleles with replacement from the candidate list and scoring a distance between the selected allelic pair and the remaining alleles, where the score of each allelic pair may be initialized at 0, and the HLA typing method may further comprise inspecting multiple sequence alignment (MSA) of the alleles obtained from the database. In such embodiments, for alleles having the same protein coding sequence, only one allele is included in the MSA, and the method may further then comprise dividing the MSA into different exons.

Some embodiments of the present disclosure are directed to a computer-implemented method for HLA typing which may include one or more of the following steps (and in some embodiments, a plurality of such steps, and in some embodiments, all such steps): accessing sequencing data that contains HLA information, filtering the sequencing data against known allelles of one or more HLA genes to obtain a first set of reads/read-pairs aligned with known HLA alleles, and assembling contigs from the first set of reads/read-pairs. Assembly may comprise filtering out reads/read-pairs aligning to known, non-target HLA alleles, merging paired-end reads, and generating contigs from merged paired-end reads. The method may further comprise identifying alleles from the contigs, where identifying may comprise dividing each allele into exons, identifying a best match for each exon in the contigs, and calculating and summing Hamming distance (HD) between contigs and known target alleles. The method may further include inferring allelic pairs, where inferring may comprise pairing candidate alleles, scoring all allelic pairs based on candidate alleles, and reporting allelic pairs with best scores.

In some embodiments, an HLA typing system is provided and comprises at least one computer having at least one processor, the at least one processor configured with computer instructions operating thereon to perform a method of HLA typing according to any such embodiments disclosed above or otherwise herein.

In some embodiments, a non-transitory computer readable medium is provided which comprises computer-executable instructions recorded thereon for causing a computer to perform one or more of the HLA typing methods disclosed above or otherwise herein.

BRIEF DESCRIPTION OF THE DRAWINGS

This application file contains at least one drawing executed in color.

FIG. 2a illustrates fold coverage at exons of each of the five target HLA genes where coverage data from all 15 samples are pooled. Median coverage (shaded lines) and range (shaded areas) are plotted over alignment positions for individual HLA genes. Dotted lines represent exon boundaries. FIG. 2b illustrate comparison of HLA typing results between an embodiment of the present disclosure and the conventional Sanger method (e.g., after only the first round of sequencing). The numbers of allelic pairs in five categories indicated are plotted for different genes of each sample. Most ambiguities encountered by Sanger sequencing are resolved only after subsequent sequencing or PCRs with sequence specific primers. For the full typing results, see FIG. 13. FIG. 2c illustrates concordance rates of HLA typing results by an embodiment of the present disclosure and HLAminer as compared with conventional Sanger-based method.

FIGS. 3a-b illustrate ambiguities resulting upon merging paired-end reads ($r_0$, $r_1$). (a) $r_0$ and $r_1$ align to $allele_0$, where the aligned regions partly overlap. The bases 300 indicate disagreement, which is denoted by a degenerate base S={G, C} in the merged read r'. With $r_2$ aligning to the same region, base C is selected in the newly merged read r''. (b) $r_0$ and $r_1$ align to both $allele_1$ and $allele_2$. $Allele_1$ contains an additional base C 300 compared to $allele_0$, within the gap between $r_0$ and $r_1$, resulting in two legitimate merging results r' and r''. r'' is supported upon the identification of an additional read $r_2$ that is consistent with r''.

FIGS. 4a-b illustrate examples of preferring similarity to length when identifying a best match of an exon and the consideration of non-zero distance alleles. Specifically, FIG. 4a illustrates the alignment of the second exons of the heterogeneous alleles A*02:01:01:01 and A*02:11:01 of sample HG01953 and the two contigs $c_i$ and $c_j$ identified by methods according to some embodiments of the disclosure. Contig $c_i$ is identical to exon 2 of A*02:01:01:01 and contig $c_j$ is a proper prefix of exon 2 of A*02:11:01. Because exon 2 of the two alleles differ only by the two bases highlighted, $c_i$ naturally serves as a candidate hit for exon 2 of A*02:11: 01 that has a length identical to exon 2 and a similarity over 99%. Nevertheless, $c_j$ is shorter but has a 100% similarity. A*02:11:01 would have been missed without tolerating missing bases. FIG. 4b illustrates the alignment of the seventh exons of candidate alleles C*04:01:01:01 and C*04: 30 and contig $c_i$ identified by methods according to some embodiments of the disclosure. $c_i$ is identical to exon 7 of C*04:01:01:01 and it is the only contig that can serve as a candidate hit for exon 7 of C*04:30. Without tolerating non-zero distance alleles, C*04:30 would have been missed.

FIGS. 5a-b illustrate an example of the determination of allelic pairs. Specifically, FIG. 5a illustrates the principle of parsimony. Assuming two contigs, $Contig_a$ and $Contig_b$, have been assembled and two candidate alleles, $allele_0$ and $allele_1$, have been identified. $Allele_0$ differs from $allele_1$ by one base, highlighted in red. In some embodiments, three allelic pairs may be checked: ($allele_0$, $allele_1$), ($allele_0$, $allele_0$) and ($allele_1$, $allele_1$). However, in some embodiments, it cannot be ruled out the possibility of ($allele_0$, $allele_0$) or ($allele_1$, $allele_1$) being the correct answer as $Contig_b$ may have supported $allele_1$ if the missing bases were TGG. However, the homozygous pair ($allele_0$, $allele_0$), in some embodiments, is preferred as it is based on the fewest assumptions and sufficient to represent both contigs. FIG. 5b illustrates that the allelic pair may capture as much information as presented in the data. For example, assuming four potential alleles (B*55:02:01, B*56:11, B*35:03:01, B*35: 60) have been identified for HLA-B of sample HG01873, for each exon of exons 1-4, two different haplotypes are present, and may be assigned with label A or B. A plurality of the alleles (e.g., all) may be supported as their individual exons are present in contigs. To that end, there are a total of 10 possible allelic combinations (4 homozygous and 6 heterozygous) of these four alleles. However, data indicates that all four exons are heterozygous, and only the pair B*55:02: 01 and B*35:03:01 result in heterozygosity (both A and B alleles) at all four exons.

FIG. 11 is a table illustrating sequences of typed HLA genes included in the reference.

FIG. 12 is a table illustrating characteristics of exome-seq data used for in silico HLA typing.

Figure 13A:
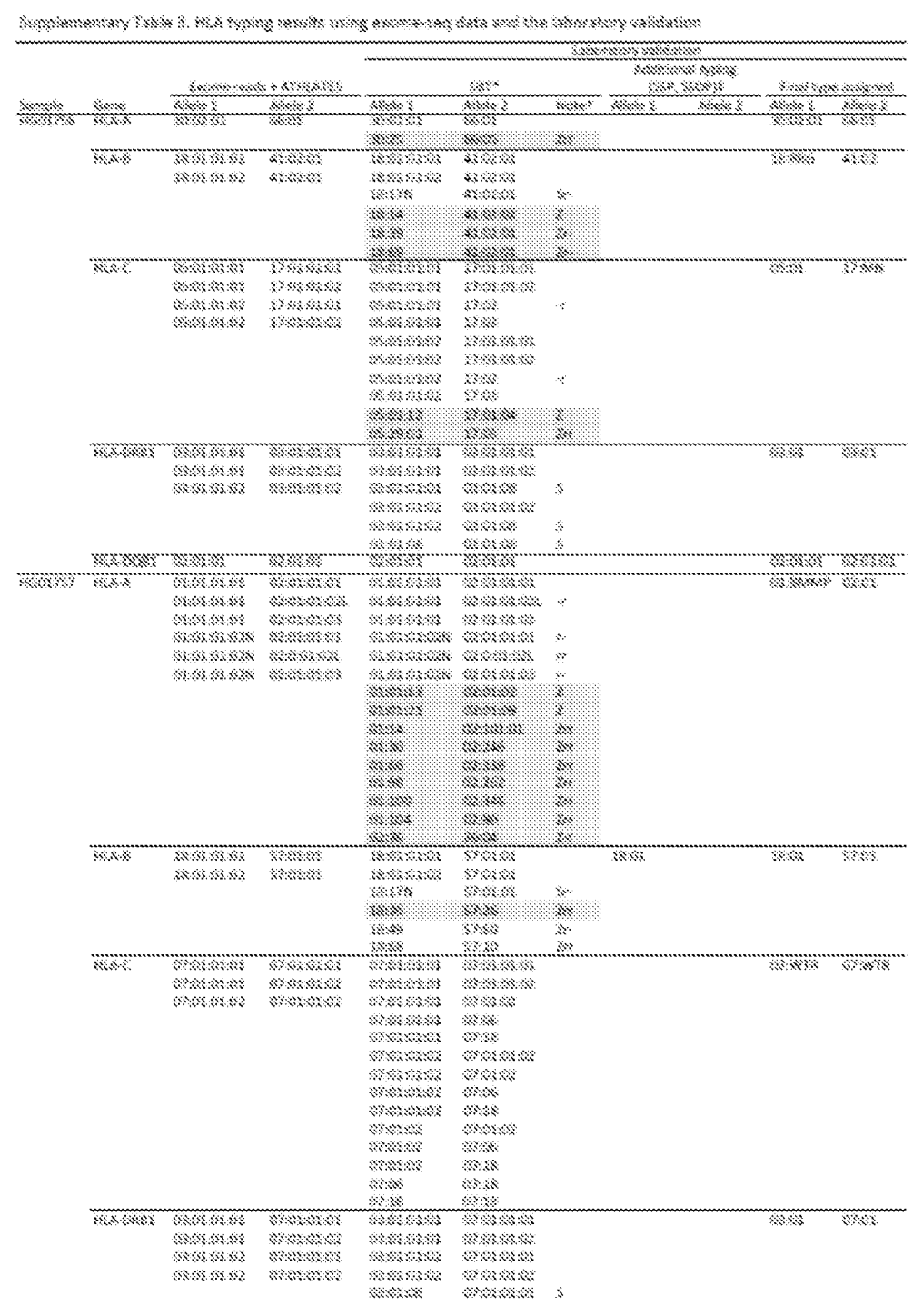
Figure 13B:
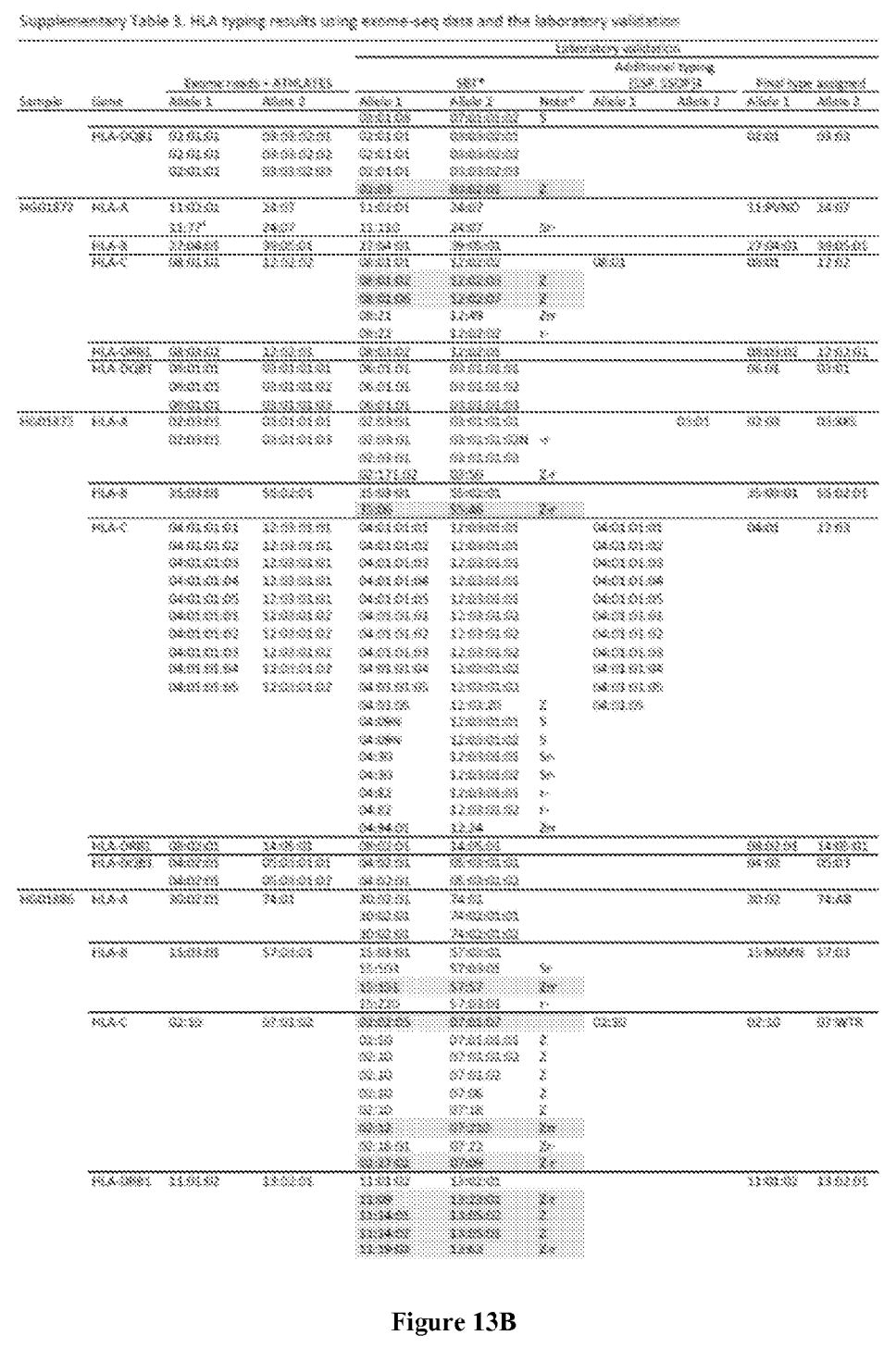
Figure 13C:
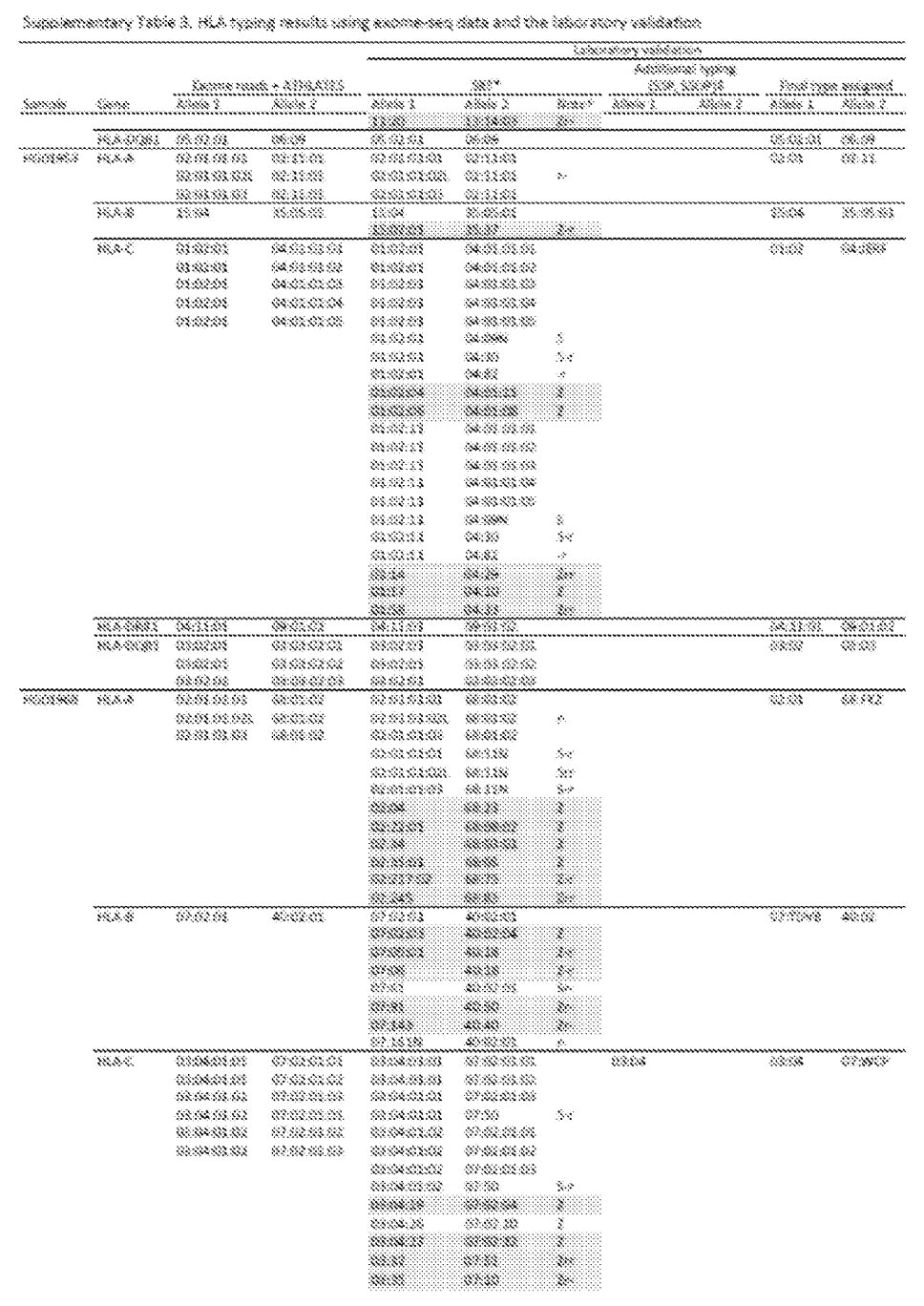
Figure 13D:
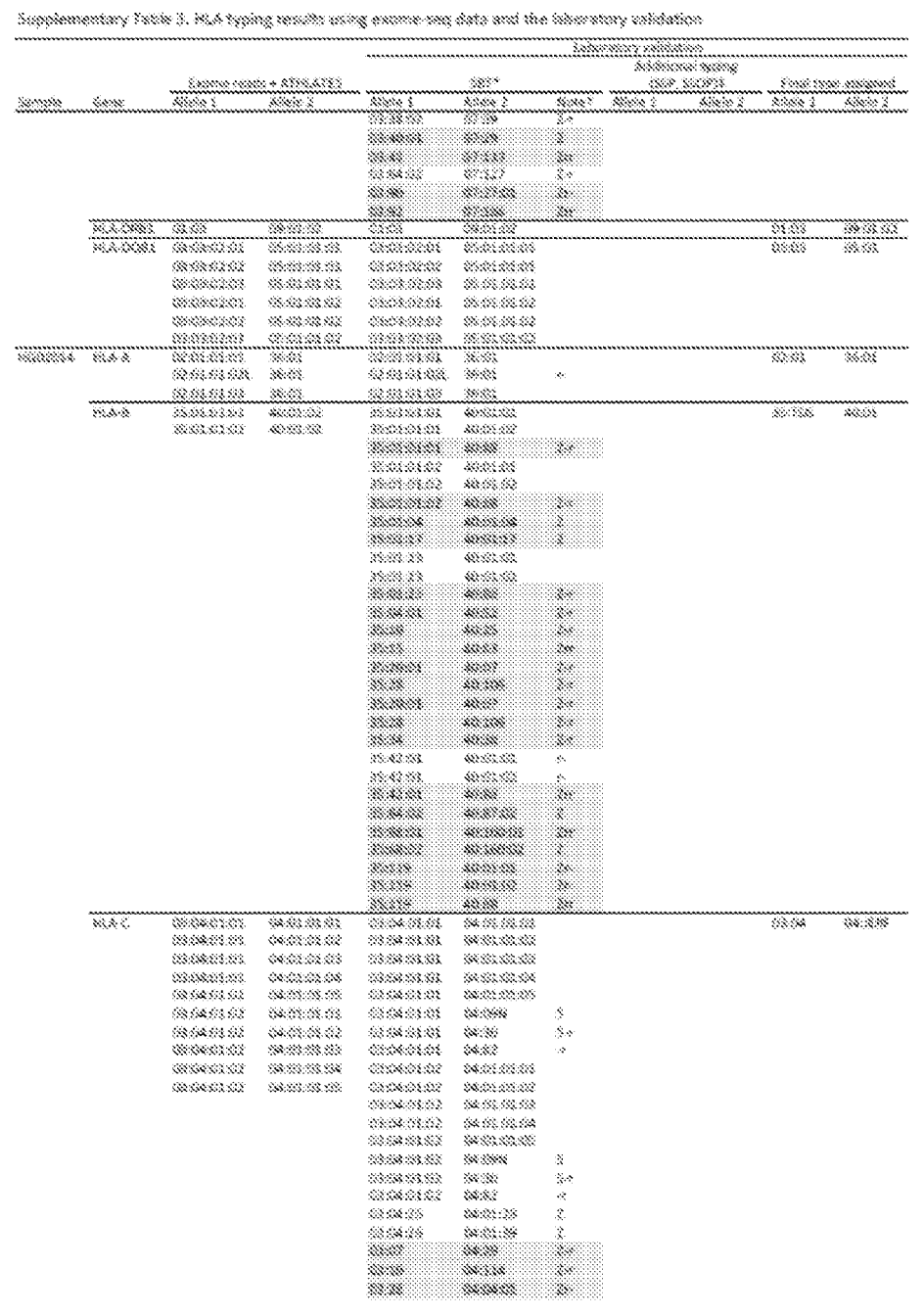
Figure 13E:
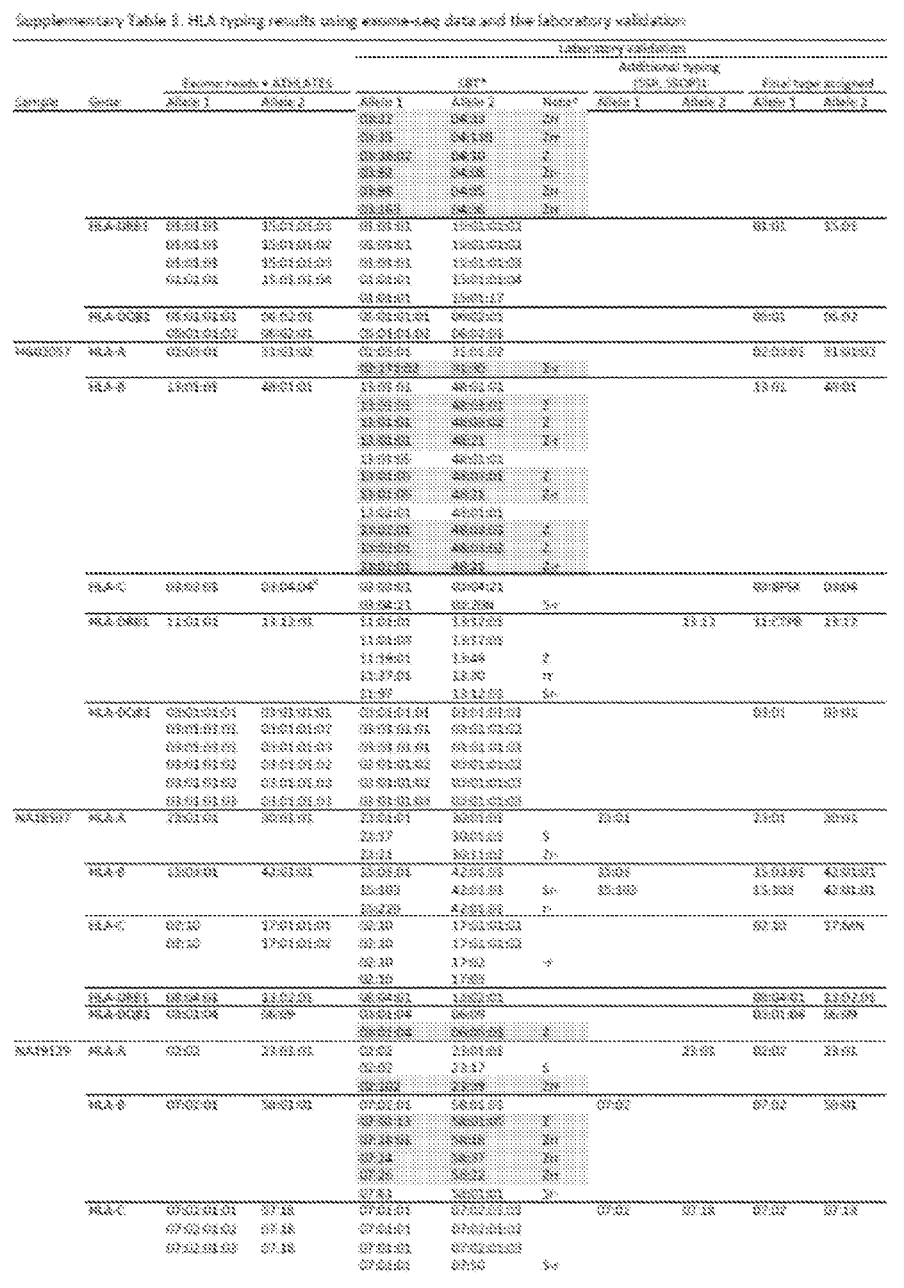
Figure 13F:
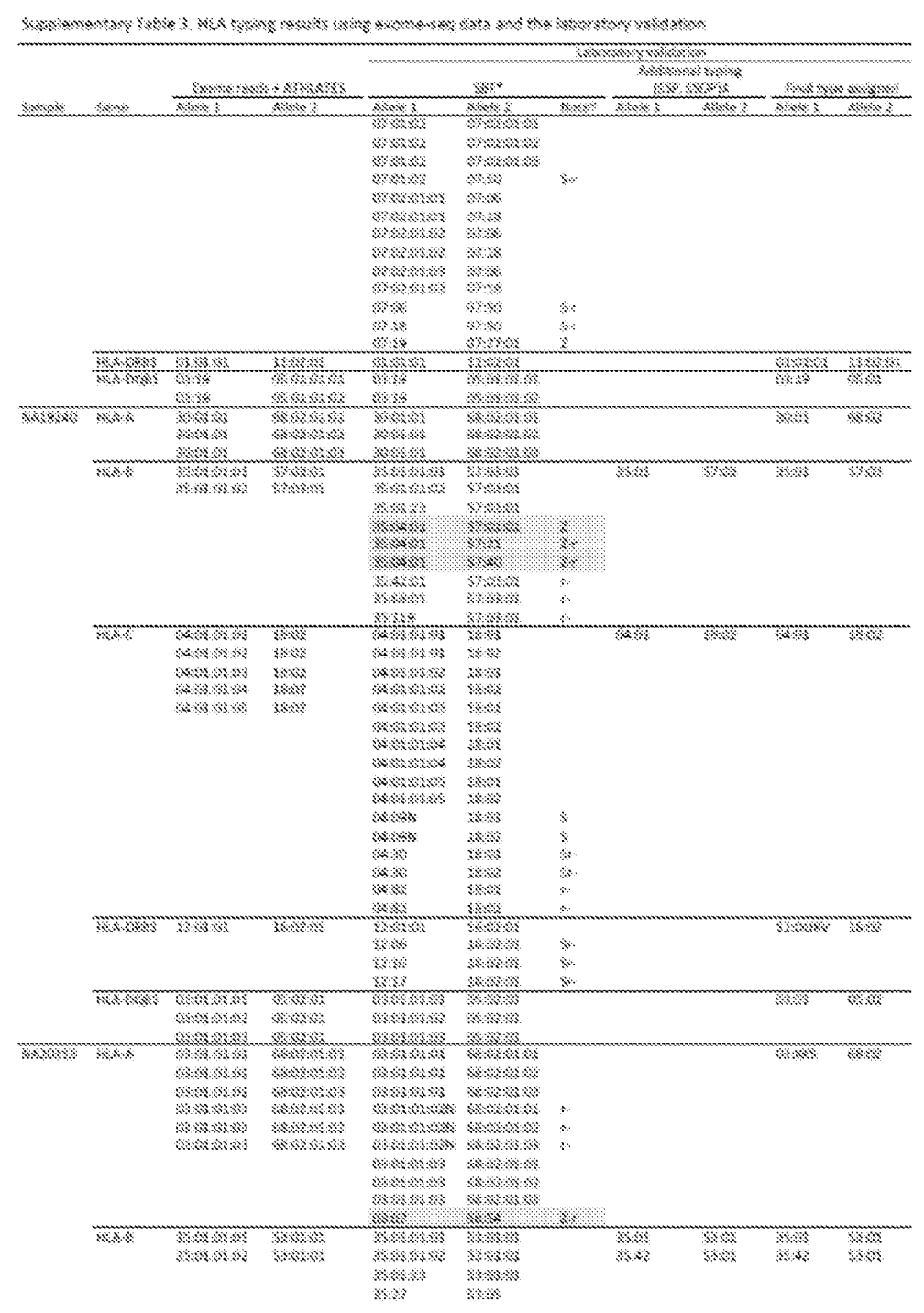
Figure 13G:
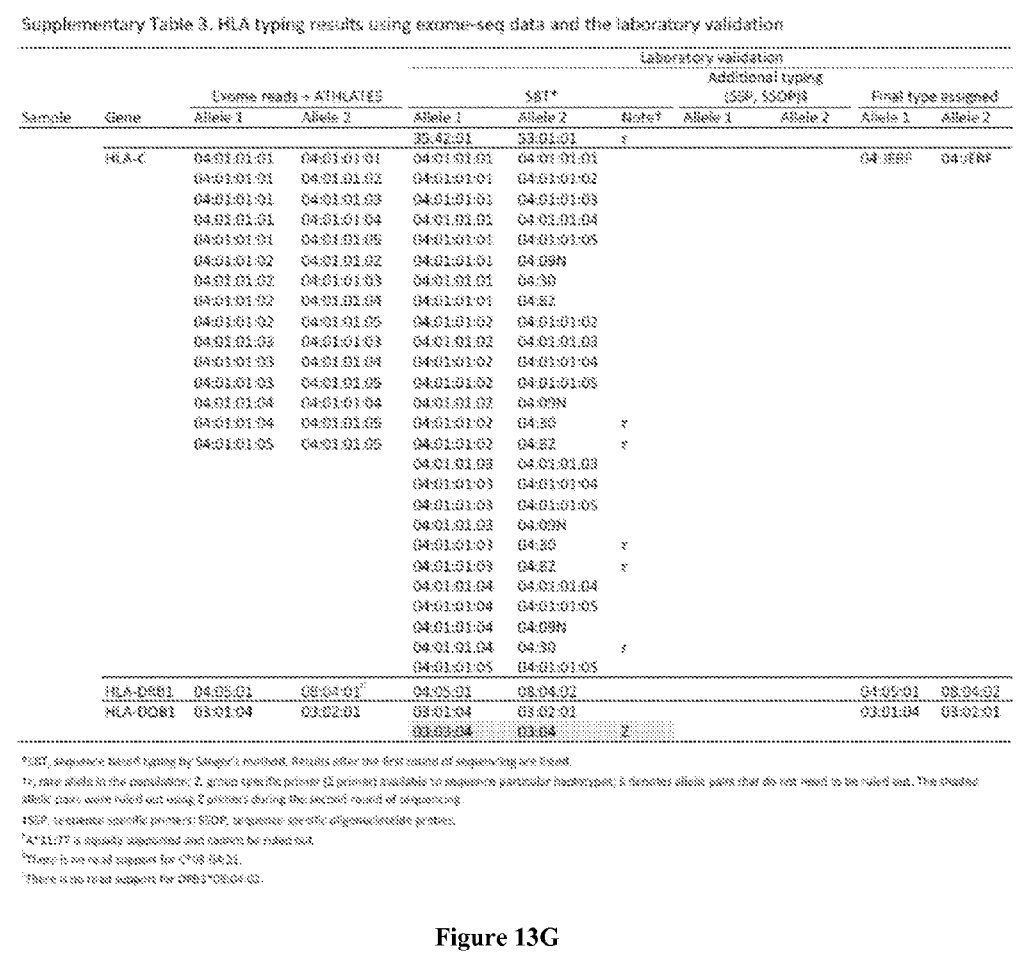

FIGS. 13a-g illustrates HLA typing results using exome-seq data and the laboratory validation.

FIG. 14 illustrates a sample report generated by an embodiment of the present disclosure.

FIGS. 15a-b illustrate a statistical analysis of allelic bias within individual exons.

FIGS. 16 and 17 represent example systems for at least one of conducting HLA typing analysis, analyzing data from such analysis, such analysis including at least one of qualifying, quantifying sequencing data, as well as including, in some embodiments, collecting and/or storing data for the analysis and/or produced as a result of such analysis.

DETAILED DESCRIPTION OF SOME OF THE EMBODIMENTS

Figure 2:
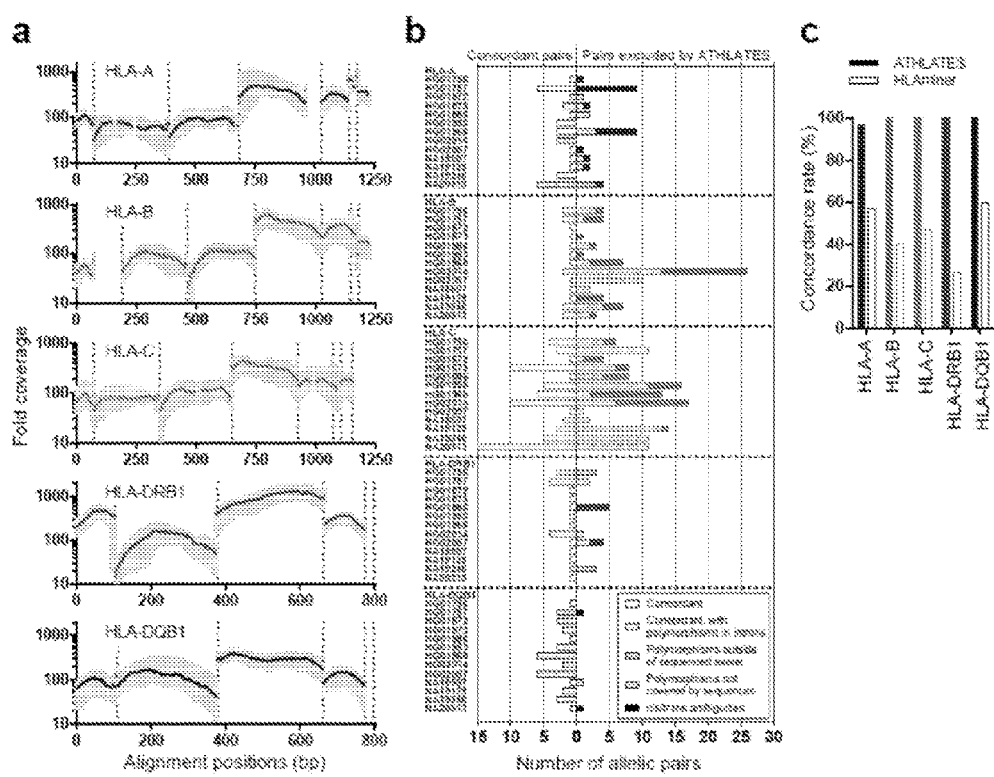
FIG. 2a-c are comparisons of HLA typing results among conventional methods (Sanger sequencing), an existing method using exome-seq data (HLAminer) and some embodiments of the present disclosure, using 15 exome-seq datasets from Illumina platforms. Specifically.
Figure 7:
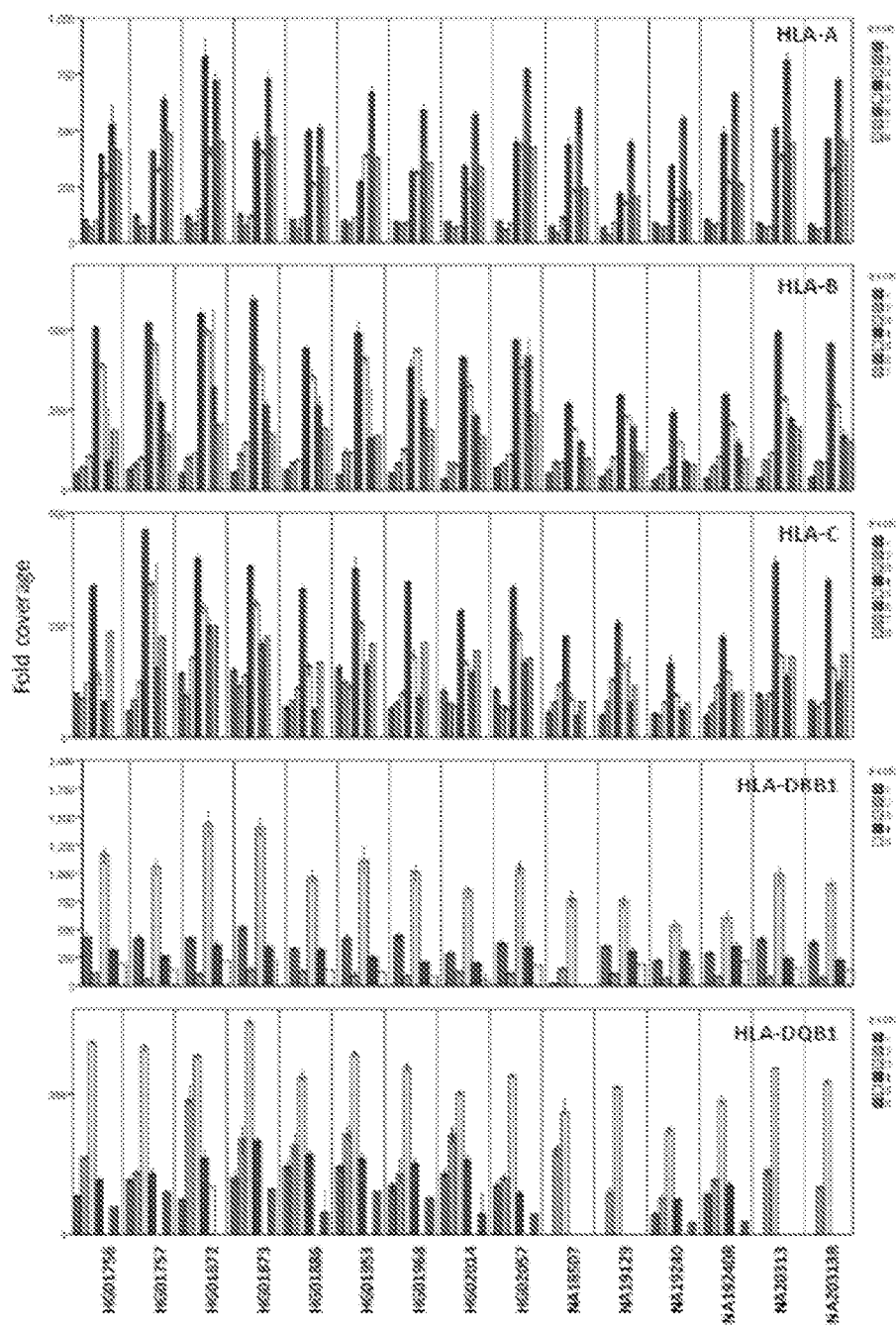
FIG. 7 illustrates variations in fold coverage among different target HLA genes and their exons. The median fold coverage is plotted for individual exons of each HLA gene. Error bars show 95% confidence intervals.

Embodiments of the present disclosure overcome a major bioinformatics hurdle in applying targeted Illumina sequencing to allelic HLA typing. Previous methods for HLA typing from traditional and next generation sequencing methods have relied on the assumption that more reads align results to the correct alleles (4) (2). However, this assumption does not wholly apply to exome-sequencing data, as there are often large differences in the coverage of different exons (FIG. 2a, FIG. 7).

Described herein are systems and methods where datasets from newly generated sequencing reads as well as datasets containing pre-existing sequence may be analyzed to captured HLA genes. In various embodiments, sequencing data may be obtained from one or more sources including, but not limited to, e.g., whole genome sequencing datasets, whole exome sequencing datasets, qualified exome-sequencing datasets, datasets obtained from deep sequencing of captured HLA genes alone rather than the whole exome, one or more sets of contigs assembled from target (e.g. HLA-A, HLA-B, HLA-C, etc.) specific reads to substantially represent haplotype exons of the target gene (in some embodiments, fully represent haplotype exons of the target gene), and/or datasets with inclusion of gDNA sequences to enhance the ability to capture reads spanning intron-exon boundaries, and, alternatively, wherein gDNA sequences may include additional sequences where capture probes for HLA introns are included In some embodiments, the sequencing datasets may comprise HLA genes bundled, e.g., with existing oncogene panels (3) for targeted Illumina sequencing, e.g., in order to prepare leukemic patients for transplantation while characterizing the molecular profiles of their diseases.

Figure 1:
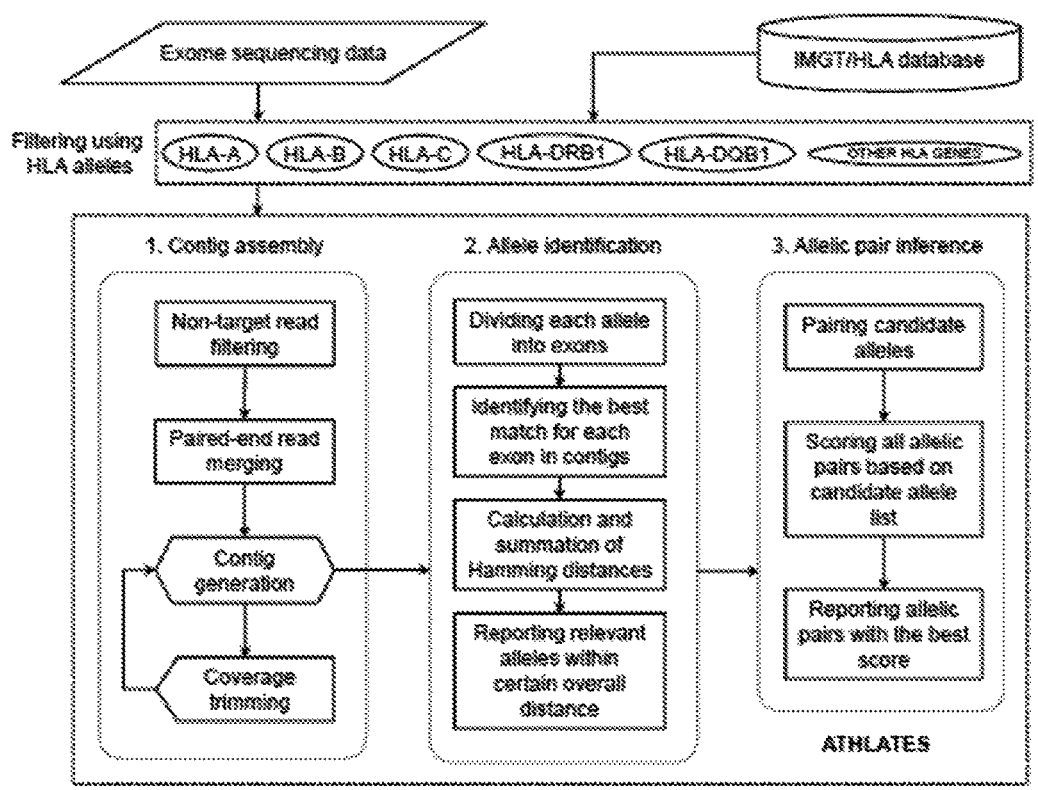
FIG. 1 is a workflow of allelic HLA typing using exome-seq data according to some embodiments of the present disclosure.
Figure 6:
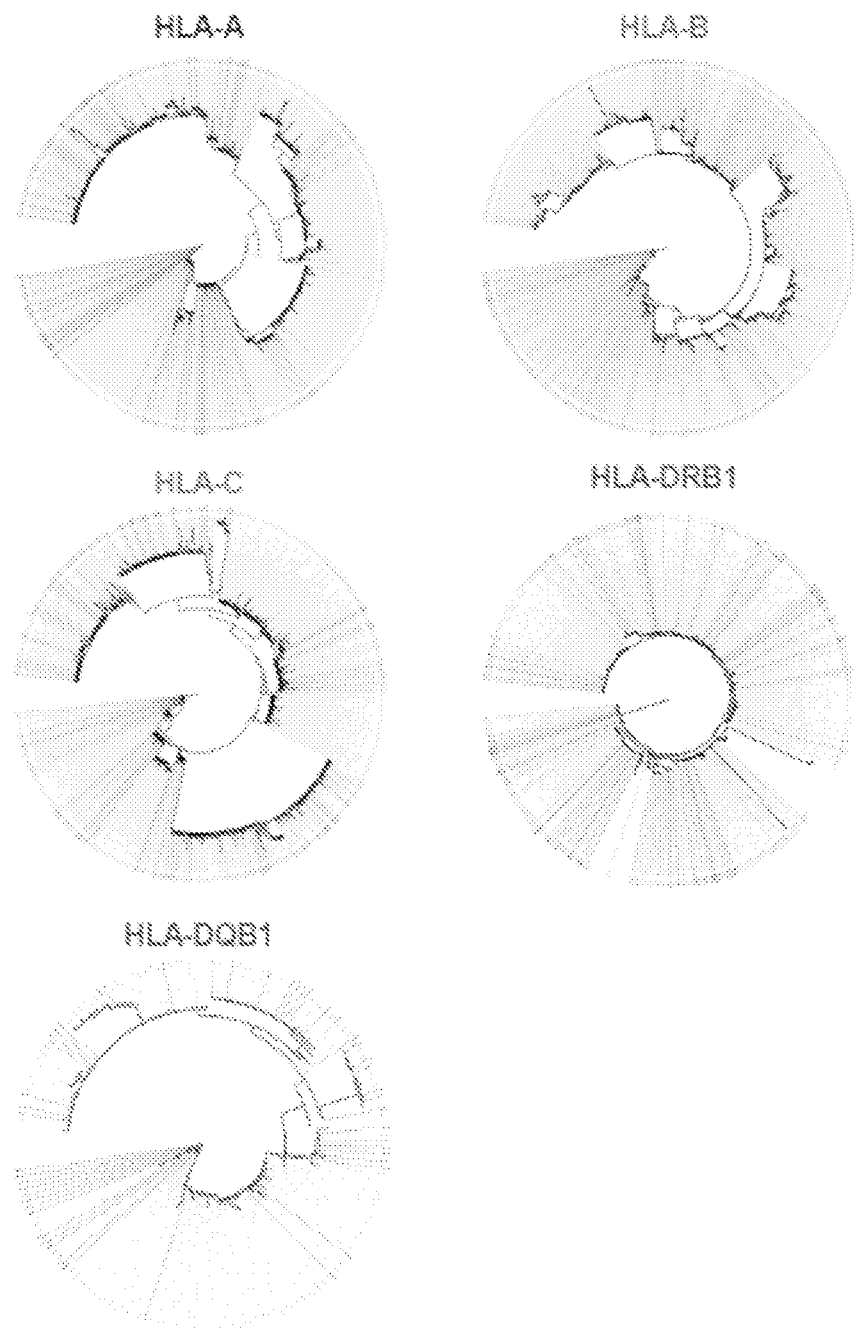
FIG. 6 illustrates the diversity of the HLA genotypes of included samples. The HLA genotypes of 13 samples included in a study are mapped onto the phylogenetic trees of known alleles of HLA-A, -B, -C, -DRB 1 and -DQB 1 genes generated using RAxML (v.7.3.3). The alleles at the four-digit resolution are highlighted in color corresponding to each gene.
Figure 8:
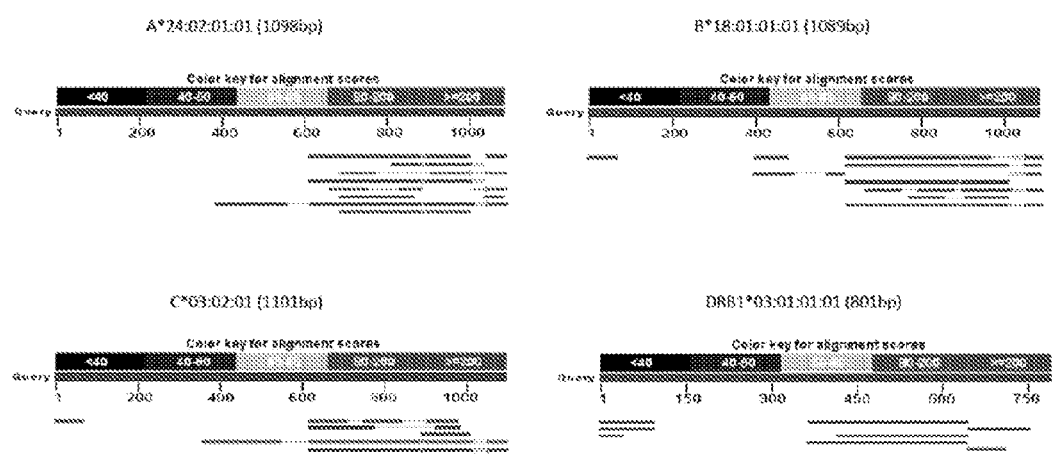
FIG. 8 illustrates an example of exom-seq data of the individual NA18526, according to some embodiments, that has inadequate coverage over target HLA genes. The five target HLA genes of this individual were typed previously. In some embodiments, no typing result may be reported for any of the target gene as the assembled contigs may not unambiguously support any candidate allele due to insufficient exon coverage. The alignment, in some embodiments, is generated using BLAST between contigs of a target gene and one of the known cDNA sequences of this gene. In certain experiments, for DQB1 gene, no contig was produced. HLAminer, on the other hand, reported typing results for HLA-A, B, C and DRB 1 genes, all of which are discordant with the known type except HLA-B, where the known type is among one of the seven equally supported candidates. 4 other samples with inadequate coverage are HG01515, HG01049, HG00731 and NA18605.
Figure 9A:
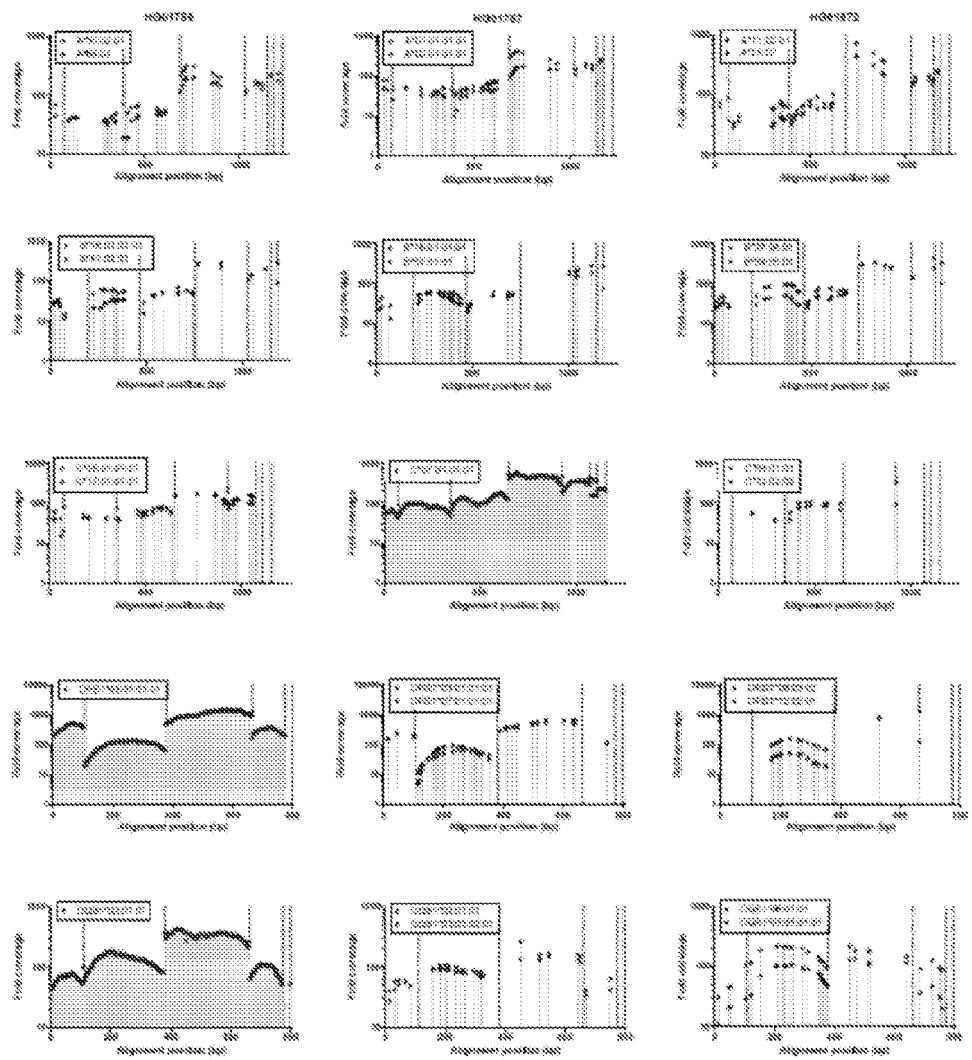
FIGS. 9a-e illustrate differential fold coverage at variant positions between validated allelic pairs for each individual. The fold coverage is plotted for each allele of a heterozygous allelic pair at positions where they differ. In case of homozygosity, the coverage is plotted for all alignment positions. Dotted lines are exon boundaries.
Figure 9B:
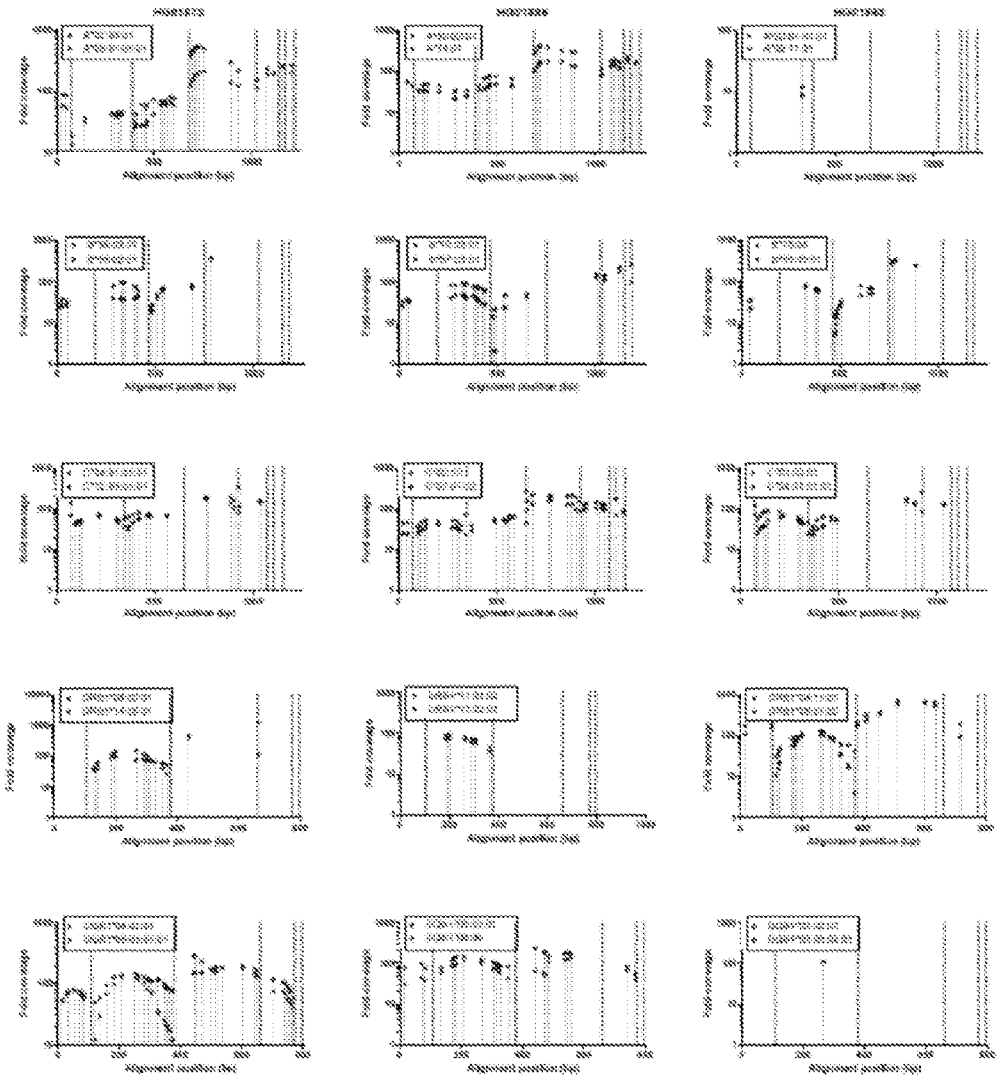
Figure 9C:
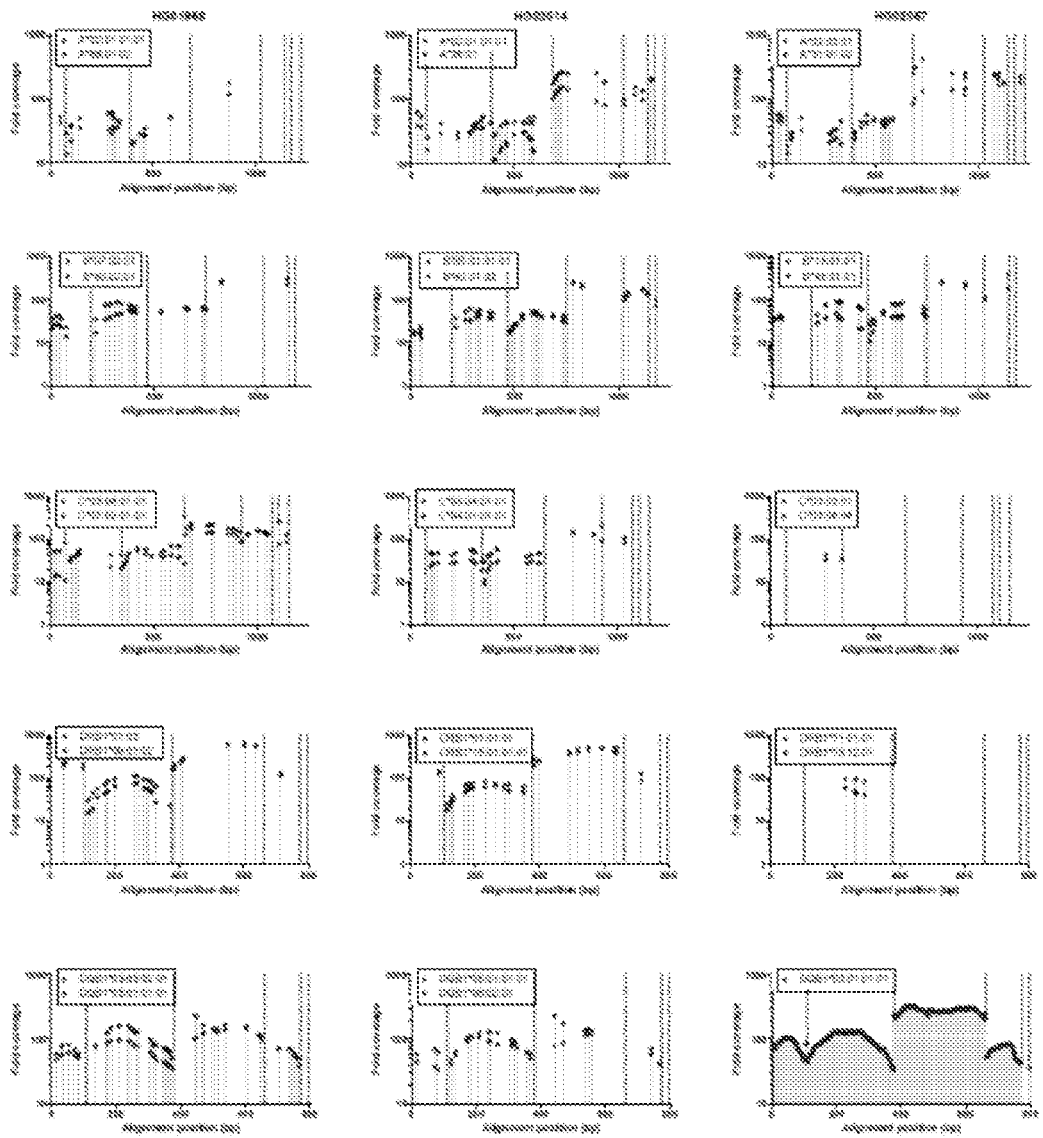
Figure 9D:
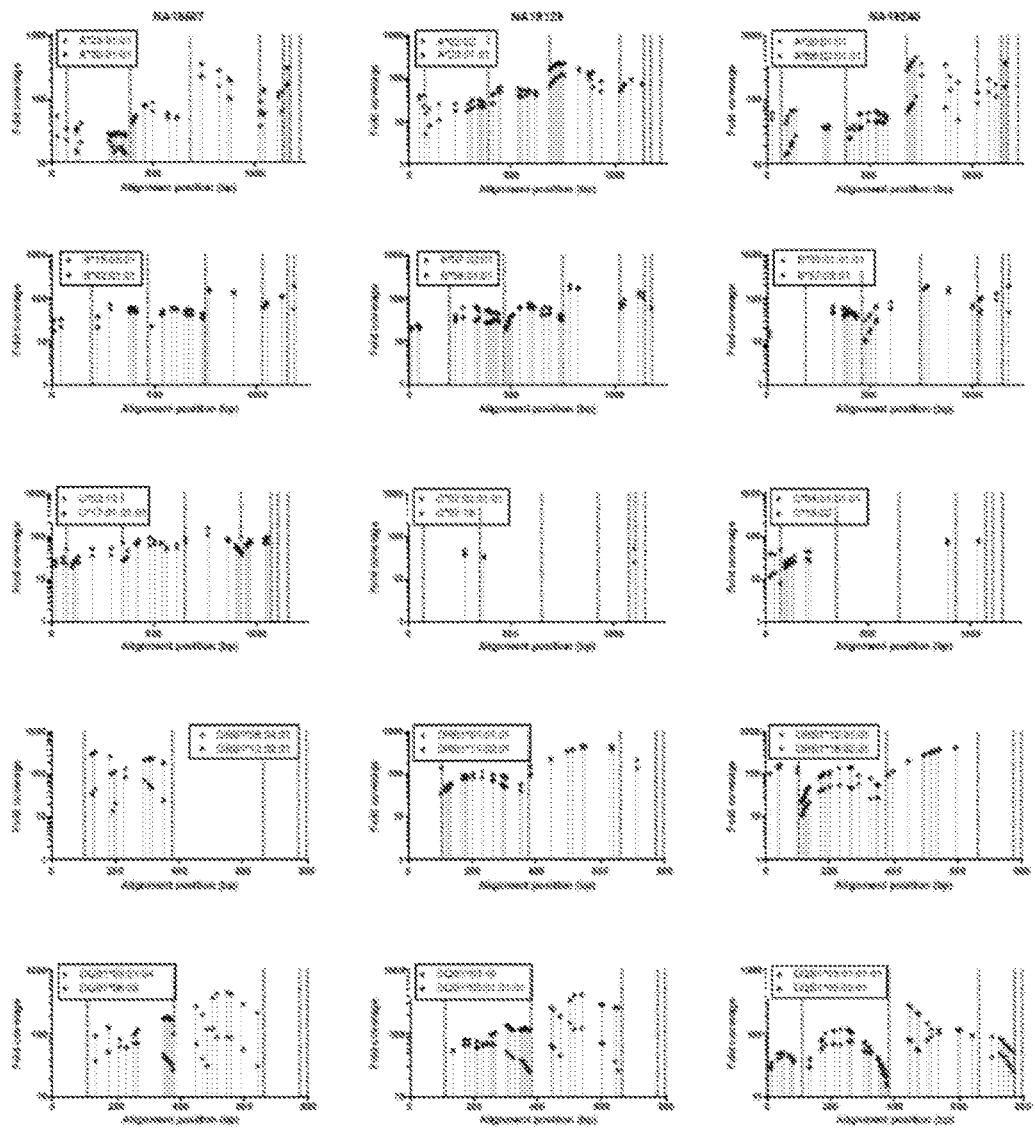
Figure 9E:
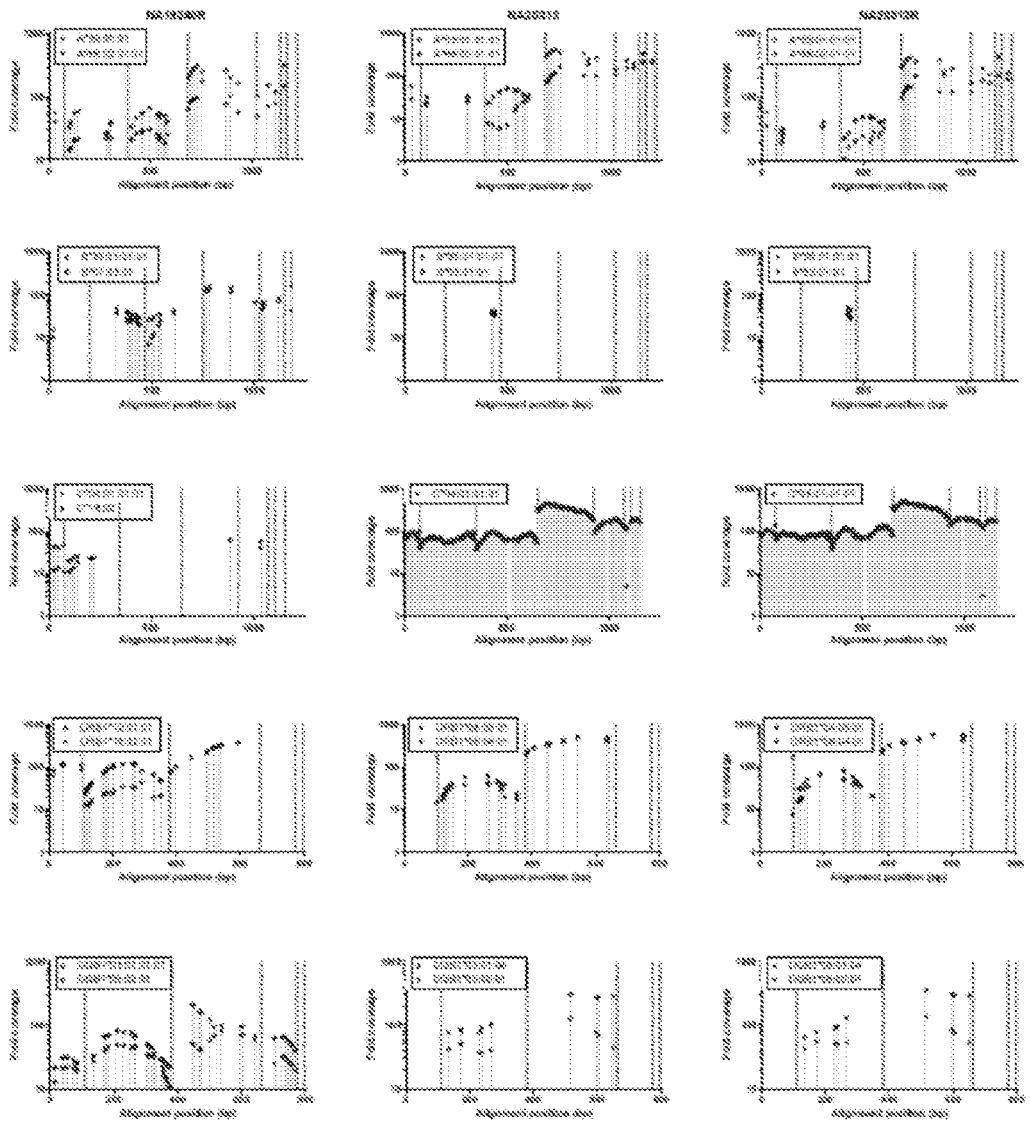

A high-level overview of a process for HLA typing according to some of the embodiments of the present disclosure is provided in FIG. 1. Accordingly, some embodiments of the present disclosure were utilized in (and will be illustrated with respect to) an example experiment to derive allelic HLA types, and will be disclosed with specific details provided below. In the example, the HLA types were derived from 15 Illumina exome-sequencing datasets: 13 subjects of five ethnicities, with two datasets are duplicates (obtained from multiple sources, including the 1000 Genomes Project (7)). The characteristics of the datasets and diversity of included HLA types are summarized in FIG. 12 and FIG. 6, respectively. Briefly, after read filtering, the median coverage of different exons of individual genes ranged from approximately ten to a thousand fold (FIG. 2a). The coverage decayed towards exon boundaries and varied significantly among exons (FIG. 7), which may be likely due to bias toward certain exons during exome capturing. In the embodiment utilized in the example, datasets lacking coverage at informative exons (FIG. 8) were rejected with no alleles or allelic pairs reported.

For the datasets, the HLA typing method (according to some embodiments of the disclosure) efficiently identified allelic pairs. Specifically, at a resolution that tolerates synonymous mutations in coding sequences, 74 out of 75 allelic pairs were correctly reported at an overall concordance rate of 99% compared with conventional typing (FIG. 13). In the example, the only case of discordance occurred to HLA-A of HG01872, where in addition to the correct allelic pair, one more pair with one base difference was reported. Interestingly, reads support for both exist in the exome-seq data.

In the example, the advantage of clonal sequencing was also harnessed to distinguish cis/trans ambiguities encountered during Sanger sequencing (which are traditionally resolved by additional sequencing or PCR with sequence specific primers). Moreover, polymorphisms were detected in exons not covered by conventional methods, and the system/method was able to exclude additional allelic pairs (FIG. 2b and FIG. 13). A report was produced providing results of the example (FIG. 14).

As noted above, for the illustrative example, the exome-seq data comprised fifteen (15) exome-seq datasets from 13 subjects were analyzed, including two duplicate sequencing datasets for two subjects (NA19240 and NA20313). The sources of these data are the 1000 Genomes Project (11 datasets; available at ftp://ftp-trace.ncbi.nih.gov/1000genomes/ftp/data/) and an internal validation project at Genome Technology Access Center (GTAC) at Washington University (four datasets; available upon request). The ethnicities of the subjects and Run ID of the datasets are listed in FIG. 12. The protocols for library preparation and exome capture were described previously (8). The protocols for the internal validation project at GTAC were similar, except that 3 μg of DNA was used as input, 6 cycles of PCR were performed to enrich for proper adaptor ligated fragments, and the Agilent SureSelect Human All Exon v.2 kit was upgraded to v.3 kit. Sequencing was performed on Illumina platforms as 2×101 bp pair-end reads, and the read count and coverage data for all samples are listed in FIG. 12.

Figure 10:
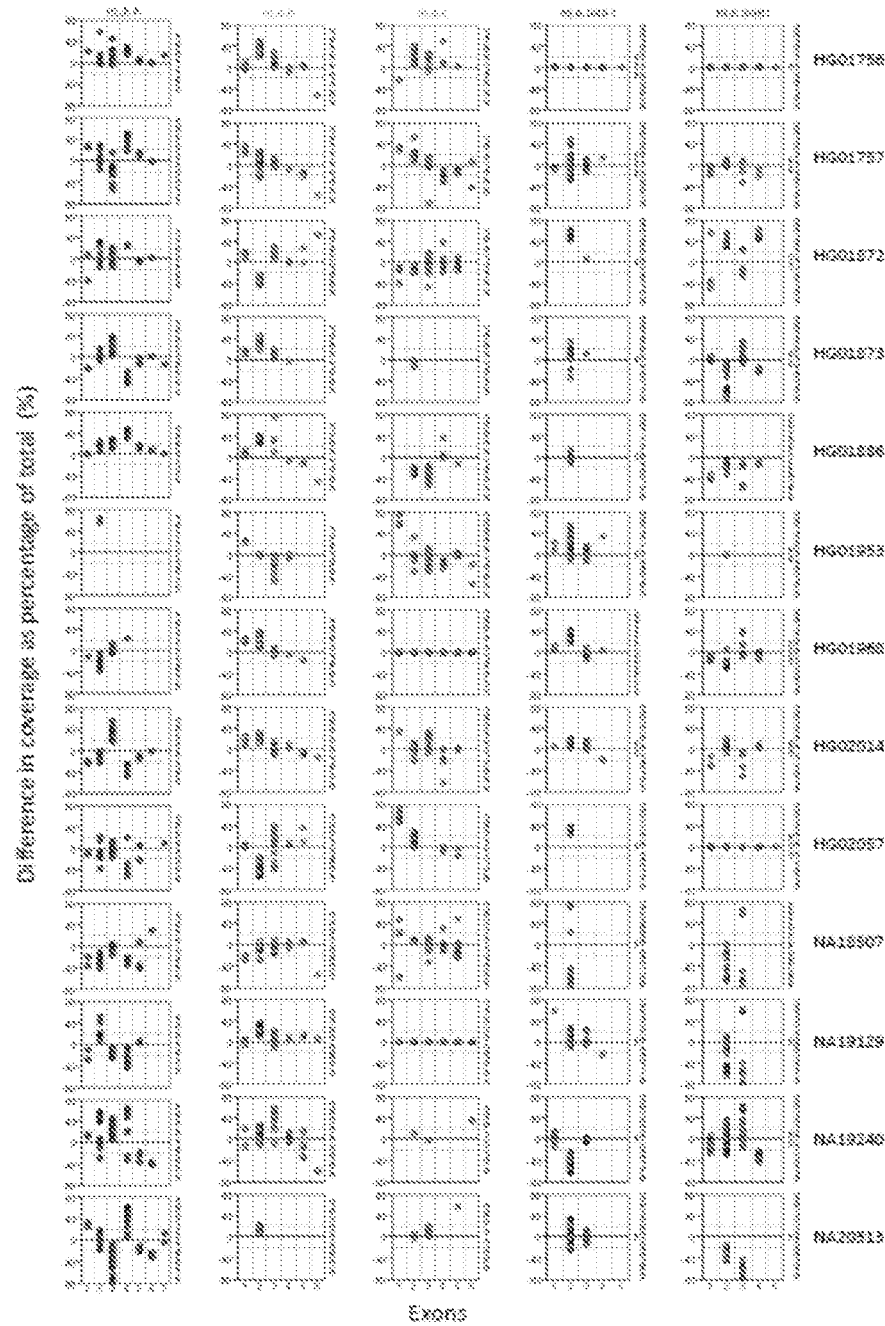
FIG. 10 illustrates a size of allelic bias in discrete exons. Differences in fold coverage between two heterozygous alleles at each variant position are plotted as the percentage of total coverage at the same variant position. Results are shown for different exons and genes of each sample; involved allelic pairs are shown to the right of each panel.
Figure 15A:
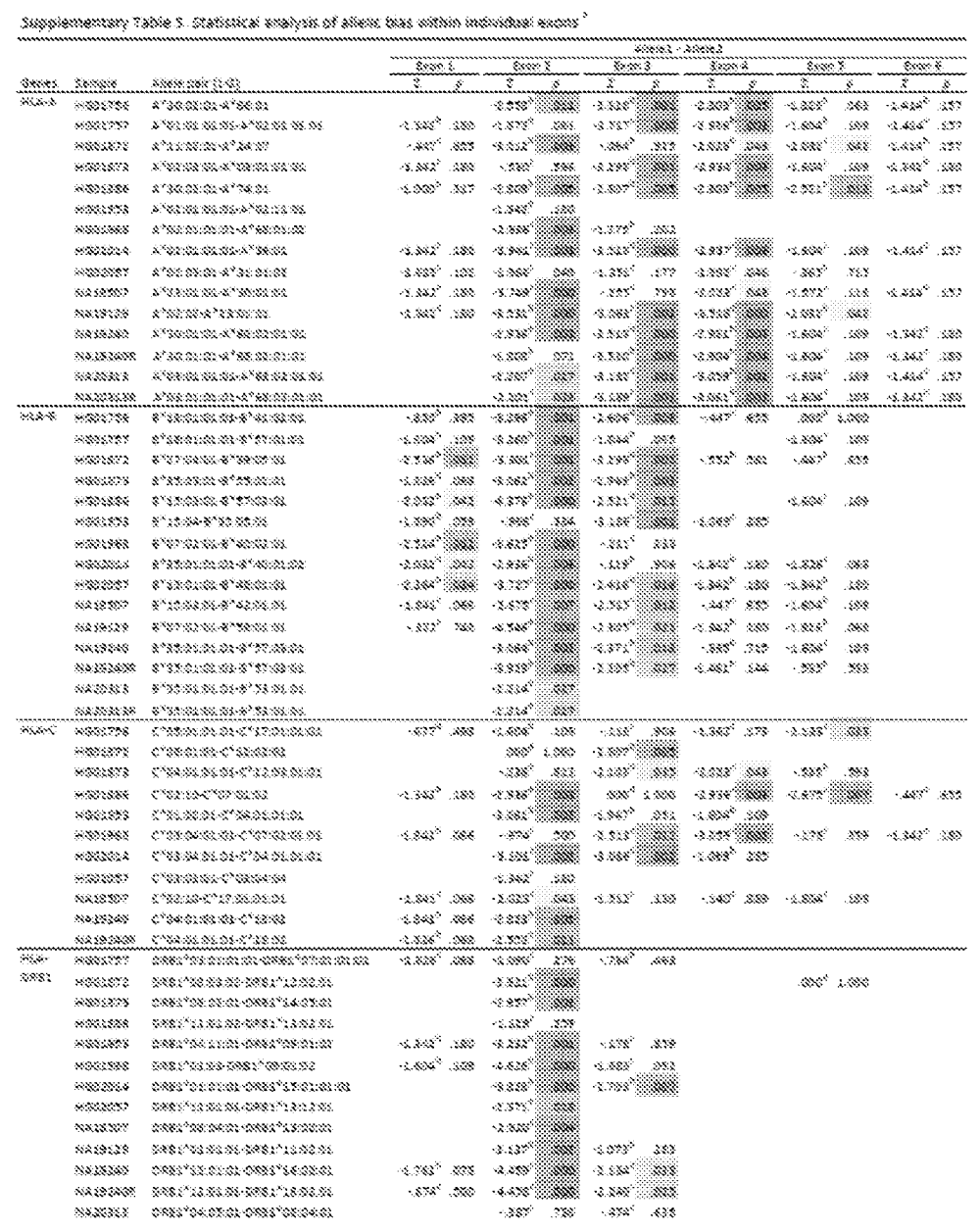

As sequencing of captured exons is susceptible to allelic bias (9), the coverage of heterozygous alleles at positions where they differ from each other was compared (FIG. 9 and FIG. 15). Statistically significant allelic biases are most frequently observed at exons 2 through 4 of Class I genes and exon 2 of Class II genes, and neighboring exons can also exhibit preference to different haplotypes. The patterns of allelic bias are highly reproducible in the two replicates examined. Almost all the bias at individual variant positions (99%) are within 80% of the total coverage (FIG. 10). In some embodiments, this does not affect the HLA typing.

It is worth noting that exome-seq data do not cover polymorphisms within introns (FIG. 2b); while this information is rarely necessary in current practice, in some embodiments it can be obtained if capture probes for HLA introns are included.

In some embodiments, where no allelic pairs are reported from datasets with adequate coverage, clues from reported relevant alleles can be further investigated by Sanger sequencing (for example).

Accordingly, provided below are additional details for a method of HLA typing, according to some embodiments, which was used for the noted example.

Scouting for Target-Specific Reads/Read-Pairs.

Initially, exome sequencing data may be aligned against a multi-FASTA file that contains all known alleles of HLA genes available from the IMGT/HLA database (FIG. 11). The inclusion of gDNA sequences enhances the ability to capture reads spanning intron-exon boundaries, although they are available for only a fraction of alleles in the database, To account for this, soft-clipping is done during alignment. Specifically, in some embodiments, it is sufficient to retain a read when it has a high quality suffix-prefix alignment with cDNA sequences. In the present example, Novoalign (http://www.novocraft,com/main/index.php) was used as the aligner, where no more than one edit distance was allowed. Information is kept when a read or read pair is aligned to multiple HLA genes.

The alignment result is recorded in a compressed BAM format, from which reads/read-pairs aligned to a target HLA gene (e.g. HLA-A) with a customized BED file registering all alleles of this gene are extracted. Likewise, reads/read-pairs that aligned to non-target genes (e.g. all non-HLA-A genes in the reference) are extracted in the same manner.

Assembly.

Reads/read-pairs uniquely aligned to the target gene may be used in the assembly step. They are first oriented to be consistent with the alignment so that their reverse complementary strands need not be considered. Paired-end reads aligned to the same reference allele are merged to form single reads based on the following method (for example): let a paired-end reads $(r_0, r_1)$ that aligned to the same allele be divided into substrings $(r_0^p, o_0, r_1^s, o_1)$, where $r_0^p$ and $r_1^s$ denote the prefix and suffix of $r_0$ and $r_1$ that do not overlap in the alignments, whereas $o_0$ and $o_1$ denote the overlapping substrings. Note that in some embodiments, $o_0$ and $o_1$ should be equal in length. When $o_0$ and $o_1$ are not empty, they may be merged to form string $o_m$, where the IUPAC (International Union of Pure and Applied Chemistry) characters, or degenerate bases, may be used to encode two different nucleotides merging at a position with one of them being a possible sequencing error. When $o_0$ and $o_1$ are empty, the sequencing gap between $r_0^p$ and $r_1^s$ may be encoded with degenerate bases 'N'. Due to the existence of alleles that contain length polymorphisms (i.e. indels), the fragment length for certain read pairs may not uniquely be determined. The uncertainties regarding the degenerate bases and fragment length may be resolved by identifying additional fragments that are likely to be obtained from the same genomic location during assembly (FIG. 3).

Reads containing sequencing errors may contain low frequency k-mers (substrings with length k set to be half of the read length) that occur only once or twice in the data(6). Since such reads may also belong to non-target genes in exome sequencing, they may be excluded from assembly rather than being corrected.

Each read may then be initialized to be a contig, and the base frequency may be recorded at each position. Assuming that contigs sharing longer substrings are more likely to be from the same haplotype, the comparison of contigs sharing longer substrings, in some embodiments, is prioritized. High-frequency substrings may also, in some embodiments, be inspected first, as haplotype sequences, such as exons with a higher read support, can be recovered more reliably. Specifically, contigs may be merged if they share common l-mers, Where l may be initially set to the value of the maximum read length and then may be iteratively decreased by a fixed amount until a minimum threshold (e.g., default of 40) is reached. For each l contigs may be decomposed into a set of l-mers, and may be sorted in a decreasing order of frequency. For each l-mer in the sorted list, contigs sharing this l-mer through alignment may be assembled, in which the relative positions of any two contigs can be determined in constant time by matching the l-mer. Because insertion/deletion errors are rare in Illumina sequencing, when generating the full alignment, they may be disallowed. In some embodiments, two contigs may be merged only if they are concordant at each alignment position. In some embodiments, if degenerate bases in IUPAC code are present, their intersection should not be empty and the base present in this intersection may be used in the assembled contig.

Meanwhile, in some embodiments, the base frequency for each position is accrued. This may be used later to identify regions of a contig with low base support ($\leq 2$) that may result from insufficient exon capture or sequencing errors. As such regions do not provide reliable haplotype sequence information and may prevent further contig merging, they may be replaced with degenerate base 'N'. The prefix or suffix of a contig that consists of a string of Ns may then be trimmed, whereas internal and intermittent Ns may be retained. Further contig merging is sought, when possible, by repeating the above steps. To track the removal of existing contigs and the creation of new ones, a union-find algorithm may be used.

Identification of relevant alleles. With adequate coverage, target exons, in some embodiments, are expected to be well represented by assembled contigs. Next, each allele of a target gene may be decomposed into exons, for which the best hit may be identified (i.e. a matching substring) among the contigs. The quality of a hit may be determined by at least one of the length and similarity (and in some embodiments, both) of matched substrings. A shorter hit with a higher similarity, in some embodiments, may be considered to have a higher quality (FIG. 4). Hamming distance may be used to quantify the differences between an exon and its hit. In some embodiments, hits covering a minimum percentage of an exon (default 85%) and within a maximum Hamming distance of 2 are considered (for example). Then, an overall distance may be calculated for each allele by summation of Hamming distances between all its exons and their best hits in the contigs. An ideal candidate allele, in some embodiments for example, should have a Hamming distance of zero. However, a true allele may have a non-zero distance for several reasons (for example): (1) small exons and part of long exons may not be effectively captured in exome sequencing (FIG. 4), and/or (2) the subject may have a novel allele with a small number of mutations compared to a known allele. Therefore, in some embodiments, it is reasonable to consider all alleles within a distance threshold (default 2). Although the threshold is an adjustable parameter (e.g., by the user), a higher threshold is unlikely to be meaningful as many known alleles have almost identical protein coding sequences. Note, the following situations may be excluded from calculation of the overall Hamming distance: (1) incompletely documented short exons (≤25 bp) and/or (2) exons with no hits in the contigs. These exclusions may prevent unjustified penalties on partially sequenced alleles in the database, or loss of novel alleles bearing inserted or deleted bases that inflate the Hamming distance dramatically when compared to a known allele. For each candidate allele identified, the following information may be reported: (1) exonic positions of mismatch compared to the best hit, termed U (stands for unsupported) positions, (2) exonic positions not fully covered by the best hit, termed M (stands for missing) positions, (3) total length of the covered region, and/or (4) the short exons excluded from distance calculation.

Inferring Allelic Pairs.

Although all alleles conforming to the distance constraint may be reported, in some embodiments, a subset may be chosen as the candidate list to represent the input data: an allele may be excluded from the candidate list if it contains any exon with no hit; the candidate list may comprise alleles only with distance zero on condition that they correspond to more than one type of protein coding sequences; otherwise, all alleles with distances less than or equal to one may be included in the candidate list.

Next, a plurality of alleles, for example a pair, may be chosen with replacement from the candidate list and a scoring scheme may be utilized to measure the distance between the selected allelic pair and the remaining alleles. More specifically, and for example, let the candidate list include n alleles be $(a_1, a_2, \ldots, a_n)$. The score of each allelic pair may be initialized to be zero. Next, multiple sequence alignment (MSA) of these alleles may be obtained. For alleles having the same protein coding sequence, only one of them may be included in the MSA. Then the MSA may be divided into different exons. Within each exon, a set of variable positions may be identified, i.e., alignment positions with more than one type of nucleotides. Then, subsequences specified by the variable positions may be obtained from all sequences in the MSA, which results in a list of strings $L=(s_1, s_2, \ldots, s_m)$ where m≤n. L captures non-redundant haplotype information of the exonic region. For each allelic pair $(a_i, a_j)$ with $1 \le i \le j \le n$, its score may be incremented by $$\sum_{l=1}^{m} \min(h(s_i, s_l), h(s_j, s_l)) + \delta,$$

where δ is initialized to be zero, and function h returns the Hamming distance between two strings except that, in some embodiments (1) any U position in $s_1$ may be skipped for comparison, and/or (2) for any M position in $s_i$ or $s_j$, When differs from $s_1$, δ may be increased by one. The former is to account for the fact that any unsupported base in the data preferably should not be penalized, and the latter is to penalize the bases in $s_i$ or $s_j$ lacking read coverage when differing from bases having read support in $s_j$. In addition, δ may be increased by the number of U positions in $s_i$ and $s_j$ such that a correct homozygous allele pair may have a higher score compared to an alternative. Note that when allele $a_i$ is not included in the MSA, $s_i$ may be obtained from the allele in the MSA that shares the same coding sequence with $a_i$. After the exons have been examined, the pairs with the same minimum score may be reported as the typing result.

Evaluation Measure.

In some embodiments.

In some embodiments, to measure the accuracy and to quantify the effort required to resolve ambiguities of the typing results, concordance rate may be measured. For example, let the number of inferred allelic pairs for m HLA genes be $(n_1, n_2, \ldots, n_m)$, among them $(c_1, c_2, \ldots, c_m)$ allelic pairs are consistent with the conventional typing results at four-digit level (same protein sequences from typed exons). Accordingly, the concordance rate is given by $\sum_{i=1}^{m}(c_i/n_i)/\sum_{i=1}^{m}n_i$. Any ambiguity or wrong prediction decreases this score. While the calculation of concordance rate for some embodiments is straightforward, since HLAminer does not infer allelic pairs but only assigns a likelihood score to each candidate allele, alleles with top two highest scores to be the predicted allelic pair are chosen (according to some embodiments). If more than two alleles share the same highest score, all of the possible pairing among them may be considered. When only one allele is reported, a homozygous allelic pair may be considered.

Laboratory Validation of HLA Typing.

Allelic HLA typing was performed using SeCore HLA Sequencing Reagents (Life Technologies, Brown Deer, Wis.) per the manufacturer's instructions. Briefly, exon 2-4 of HLA-A, -B and -C, exon 2 of HLA-DRB1, and exon 2 and 3 of HLA-DQB 1 were amplified in five PCR reactions followed by Sanger sequencing from both the 5' and 3' ends. Next, some cis/trans ambiguities from the first round of sequencing were resolved by sequencing one haplotype of a heterozygous allelic pair with allele specific primers, called Z primers. For HLA-DRB 1 gene, a variation at codon 86 (GGT/GTG) shows dichotomy among most HLA-DRB1 alleles, and a Z primer specific for this variation was used preemptively during the first round of sequencing to reduce cis/trans ambiguities. Data analysis was performed with uTYPE 6.0 (Life Technologies, Brown Deer, Wis.). Equivalent allele pairs were reported with letter strings specified by the National Marrow Donor Program (http://bioinformatics.nmdp.org/HLA/Allele_Codes/Allele_Code_Lists/Allele_Code_Lists. as px) and the IMGT/HLA Database(1). Cases with unresolved ambiguities were further examined by the sequence specific primer (SSP) method. This was performed using the Olerup-SSP kit (Olerup SSP AB, Stockholm, Sweden). Panels of allele specific primers were selected for genes with ambiguous typing results, and the patterns of positive PCR amplifications were correlated with specific alleles using worksheets provided by the manufacturer. In addition, sequence specific oligonucleotide probe (SSOP) hybridization was performed for all samples using the LabType SSO kit (One Lambda, Canoga Park, Calif.) on a Luminex platform (Luminex, Austin, Tex.).

Accordingly, some embodiments of the present disclosure significantly outperform HLAminer(2), the only other available program capable of HLA typing using exome-seq data. However, without read filtering, HLAminer cannot finish computation even after 10 days of running (3 datasets tested). Using filtered reads as input, HLAminer reported candidate alleles ranked by likelihood without inferring the final allelic pair(s). After testing all datasets, the estimated overall concordance rate for HLAminer was 46% compared with conventional typing results, consistent with the previous report. The performance comparison between some embodiments of the present disclosure and HLAminer for individual genes is shown in FIG. 2c.

The example experiment was executed at a workstation having a six-core 880 MHz and 2400 MHz AMD processors with 250 GB RAM running GNU/Linux x86_64. The method according to embodiments of the present disclosure finished within 2 minutes, while the experiment with HLAminer required 10 minutes to complete. Moreover, the example was performed (according to some embodiments), using the following:

HLAminer (v.1.0.5) may be used, with the script HPTASRwgs_classI-II.sh having a parameter "-i 1";

Novoalign (v.2.07.07) run on 9 cores with parameters "-t 30 -r all -l 80 -e 1 -i 230 140"; and/or RAxML (v.7.3.3) to generate phylogenetic trees with parameters "-p 78960 -f a -x 12345 -#1000 -m GTR-GAMMA".

Various implementations of the embodiments disclosed above, in particular at least some of the methods/processes disclosed, may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system according to some such embodiments described above may include clients and servers. A client and server are generally remote from each other and typically interact through a communication network. The relationship of client and server arises by virtue of computer programs running on the respective computers and having a client-server relationship to each other.

For example, as shown in FIG. 16, a processor which may include instructions operating thereon for carrying out one and/or another disclosed method, which may communicate with one or more databases—of which, may store the sequencing data required for different embodiments of the disclosure. As noted, the processor may include computer instructions operating thereon for accomplishing any and all of the methods and processes disclosed in the present disclosure. Input/output means may also be included, and can be any such input/output means known in the art (e.g., display, printer, keyboard, microphone, speaker, transceiver, and the like). Moreover, in some embodiments, the processor and at least the database can be contained in a personal computer or client computer which may operate and/or collect data from the sequencer. The processor also may communicate with other computers via a network (e.g., intranet, internet, VPN).

Similarly, FIG. 17 illustrates a system according to some embodiments which may be established as a server-client based system, in which the client computers are in communication with databases, and the like. The client computers may communicate with the server via a network (e.g., intranet, internet, VPN).

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, any logic flow depicted in the accompanying figures and described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to HLA typing. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure).

REFERENCES

1. Robinson, J., Mistry, K., McWilliam, H., Lopez, R., Parham, P. and Marsh, S. G. (2011) The IMGT/HLA database. *Nucleic Acids Res,* 39, D1171-1176.
2. Warren, R. L., Choe, G., Freeman, D. J., Castellarin, M., Munro, S., Moore, R. and Holt, R. A. (2012) Derivation of HLA types from shotgun sequence datasets. *Genome Med,* 4, 95.
3. Spencer, D. H., Abel, H. J., Lockwood, C. M., Payton, J. E., Szankasi, P., Kelley, T. W., Kulkarni, S., Pfeifer, J. D. and Duncavage, E. J. (2013) Detection of FLT3 Internal Tandem Duplication in Targeted, Short-Read-Length, Next-Generation Sequencing Data. *J Mol Diagn,* 15, 81-93.
4. Wang, C., Krishnakumar, S., Wilhelmy, J., Babrzadeh, F., Stepanyan, L., Su, L. F., Levinson, D., Fernandez-Vina, M. A., Davis, R. W., Davis, M. M. et al. (2012) High-throughput, high-fidelity HLA genotyping with deep sequencing. *Proc Natl Acad Sci USA,* 109, 8676-8681.
5. Butler, J., MacCallum, I., Kleber, M., Shlyakhter, I. A., Belmonte, M. K., Lander, E. S., Nusbaum, C. and Jaffe, D. (2008) ALLPATHS: de novo assembly of whole-genome shotgun microreads. *Genome Res,* 18, 810-820.
6. Li, R., Zhu, H., Ruan, J., Qian, W., Fang, X., Shi, Z., Li, Y., Li, S., Shan, G., Kristiansen, K. et al. (2010) De novo assembly of human genomes with massively parallel short read sequencing. *Genome Res,* 20, 265-272.
7. Abecasis, G. R., Altshuler, D., Auton, A., Brooks, L. D., Durbin, R. M., Gibbs, R. A., Hurles, M. E. and McVean, G. A. (2010) A map of human genome variation from population-scale sequencing. *Nature,* 467, 1061-1073.
8. Abecasis, G. R., Auton, A., Brooks, L. D., DePristo, M. A., Durbin, R. M., Handsaker, R. E., Kang, H. M., Marth, G. T. and McVean, G. A. (2012) An integrated map of genetic variation from 1,092 human genomes. *Nature,* 491, 56-65.
9. Gnirke, A., Melnikov, A., Maguire, J., Rogov, P., LeProust, E. M., Brockman, W., Fennell, T., Giannoukos, G., Fisher, S., Russ, C. et al. (2009) Solution hybrid selection with ultra-long oligonucleotides for massively parallel targeted sequencing. *Nat Biotechnol,* 27, 182-189.

What is currently claimed:

1. A computer-implemented method for Human Leukocyte Antigen (HLA) typing, the method comprising:
    accessing sequencing data that contains HLA information stored in one or more databases;
    accessing HLA sequences of alleles of one or more HLA genes and the multiple sequence alignment of these HLA sequences stored in one or more databases;
    searching for target-specific reads/read-pairs from the sequencing data, wherein searching comprises:
    first filtering the sequencing data against HLA sequences to obtain a first set of reads/read-pairs aligned to these sequences; and
    second filtering the first set to eliminate reads/read-pairs concurrently aligned to both sequences of the target HLA gene and off-target HLA genes to obtain a second set of target HLA reads/read-pairs;
    assembling a plurality of reads/read-pairs uniquely aligned to a target HLA gene into one or more contigs, wherein assembling comprises:
    merging read-pairs having both ends aligned to the same reference allele to form single-reads/haplotype sequences; and
    assembling one or more contigs from the haplotype sequences, wherein assembly of contigs having longer substrings with higher frequencies is prioritized; and
    identifying relevant target alleles having exons matching the assembled contigs, wherein identifying comprises:
    decomposing target alleles into exons;
    calculating the Hamming distance (HD) between individual target allele exons and corresponding best matches from the assembled contigs; and prioritizing sequence similarity over the length of matching substrings between the contigs and the target allele exons.

2. The method according to claim 1, wherein relevant alleles within a first predetermined HD are selected as candidate alleles.

3. The method of claim 1, further comprising inferring at least one of homozygous or heterozygous allelic pairs from the candidate alleles, wherein inferring comprises selecting alleles from the candidate alleles having a HD less than a second predetermined distance.

4. The method of claim 1, wherein first filtering includes soft-clipping during alignment.

5. The method of claim 4, wherein a read/read-pair is included in the first set upon the read/read-pair having a high quality suffix-prefix alignment with the HLA sequences of known alleles.

6. The method of claim 1, further comprising dividing paired-end reads that align to the same known allele into substrings, wherein upon the prefix and suffix of the paired-end reads overlapping, and the substrings being substantially equal in length and not empty, the read-pairs are merged to form single-reads/haplotype sequences.

7. The method of claim 6, wherein upon one read of a read-pair merging at a position including a sequencing error, degenerate bases are encoded in the merged haplotype sequence.

8. The method of claim 7, wherein upon the overlap being empty, the gap between the read-pair is encoded with degenerative bases.

9. The method of claim 1, wherein assembly of the contigs from the haplotype sequences comprises merging haplotype sequences upon the haplotype sequences sharing common/-mers.

10. The method of claim 9, wherein '/' is initially set to the value of the maximum read length and then iteratively decreased by a fixed amount until a minimum threshold is reached.

11. The method of claim 1, wherein haplotype sequences containing sequencing errors comprise reads/read-pairs having low frequency &-mers, and wherein such read/read-pairs are eliminated from assembly into contigs.

12. The method of claims 1 and, wherein the sequencing data is obtained from one or more datasets selected from: whole genome sequencing datasets, whole exome sequencing datasets, qualified exome-sequencing datasets, datasets obtained from deep sequencing of captured HLA genes alone, one or more sets of contigs assembled from target specific reads to substantially or fully represent haplotype exons of the target gene, datasets with inclusion of gDNA sequences to enhance the ability to capture reads spanning intron-exon boundaries, and gDNA sequences that include additional sequences where capture probes for HLA introns are included.

13. An HLA typing system comprising a computer having a processor, the processor configured with computer instructions operating thereon to perform a method of HLA typing according to claim 1.

14. A computer-implemented method for Human Leukocyte Antigen (HLA) typing, the method comprising:
    accessing sequencing data that contains HLA information;
    filtering the sequencing data against known alleles of one or more HLA genes to obtain a first set of reads/read-pairs aligned with known HLA alleles;
    assembling contigs from the first set of reads/read-pairs, wherein assembly comprises:
    filtering out reads/read-pairs aligning to known, non-target HLA alleles;
    merging paired-end reads; and
    generating contigs from merged paired-end reads;
    identifying alleles from the contigs, wherein identifying comprises:
    dividing each allele into exons;
    identifying a best match for each exon in the contigs; and
    calculating and summing Hamming distance (HD) between contigs and known target alleles; and
    inferring allelic pairs, wherein inferring comprises:
    pairing candidate alleles;

scoring all allelic pairs based on candidate alleles; and reporting allelic pairs with best scores.

15. A computer-implemented method for Human Leukocyte Antigen (HLA) typing, the method comprising:

searching for target-specific reads/read-pairs from sequencing data, wherein searching comprises:

first filtering the sequencing data against HLA sequences to obtain a first set of reads/read-pairs aligned to these sequences; and second filtering the first set to eliminate reads/read-pairs concurrently aligned to both sequences of the target HLA gene and off-target HLA genes to obtain a second set of target HLA reads/read-pairs.

16. The method of claim 15, further comprising assembling a plurality of reads/read-pairs uniquely aligned to a target HLA gene into one or more contigs.

17. The method of claim 16, wherein assembling comprises:

merging read-pairs having both ends aligned to the same reference allele to form single-reads/haplotype sequences; and assembling one or more contigs from the haplotype sequences, wherein assembly of contigs having longer substrings with higher frequencies is prioritized.

18. The method of claim 15, further comprising identifying relevant target alleles having exons matching the assembled contigs.

19. The method of claim 15, wherein identifying comprises:

decomposing target alleles into exons;

calculating the Hamming distance (HD) between individual target allele exons and corresponding best matches from the assembled contigs; and prioritizing sequence similarity over the length of matching substrings between the contigs and the target allele exons.

* * * * *